( 12 ) United States Patent
Colas

(10) Patent No.: US 9,244,036 B2
(45) Date of Patent: Jan. 26, 2016

(54) SYSTEM AND METHOD FOR DETERMINATION OF A CONCENTRATION OF AT LEAST ONE INTERFERING SUBSTANCE AND CORRECTION OF GLUCOSE CONCENTRATION BASED ON THE CONCENTRATION OF THE INTERFERING SUBSTANCE

(71) Applicant: Cilag GmbH International, Zug (CH)

(72) Inventor: Aurelie Colas, Aberdeen (GB)

(73) Assignee: Cilag GmbH International, Zug (CH)

( * ) Notice: Subject to any disclaimer, the term of this patent is extended or adjusted under 35 U.S.C. 154(b) by 540 days.

(21) Appl. No.: 13/679,906

(22) Filed: Nov. 16, 2012

(65) Prior Publication Data

US 2014/0138261 A1 May 22, 2014

(51) Int. Cl.
*G01N 27/327* (2006.01)
(52) U.S. Cl.
CPC .................................. *G01N 27/3274* (2013.01)
(58) Field of Classification Search
CPC ................................................. G01N 27/3274
See application file for complete search history.

(56) References Cited

U.S. PATENT DOCUMENTS

| 4,772,561 | A | 9/1988 | Genshaw |
| 6,780,645 | B2 * | 8/2004 | Hayter et al. ...................... 436/8 |
| 7,653,492 | B2 | 1/2010 | Davies et al. |
| 7,749,371 | B2 * | 7/2010 | Guo et al. ...................... 205/792 |
| 2005/0133368 | A1 | 6/2005 | Davies et al. |
| 2007/0276621 | A1 | 11/2007 | Davies et al. |
| 2008/0262088 | A1 | 10/2008 | Hauck et al. |
| 2012/0255044 | A1 | 10/2012 | Matsuo et al. |

FOREIGN PATENT DOCUMENTS

| EP | 0229982 B1 | 5/1991 |
| EP | 1685393 B1 | 2/2007 |
| EP | 1678489 B1 | 4/2007 |

* cited by examiner

*Primary Examiner* — Alexander Noguerola

(57) ABSTRACT

Described are methods and systems to apply a plurality of test voltages to the test strip and measure a current transient output resulting from an electrochemical reaction in a test chamber of the test strip so that an estimated interferent value can be determined so that such interferent value can be used to correct the current transients at specific time points for more accurate glucose concentration determination.

13 Claims, 15 Drawing Sheets

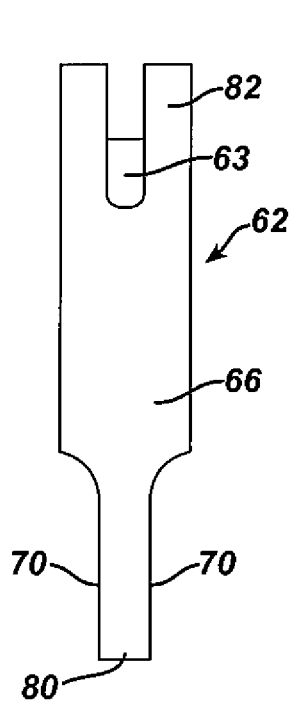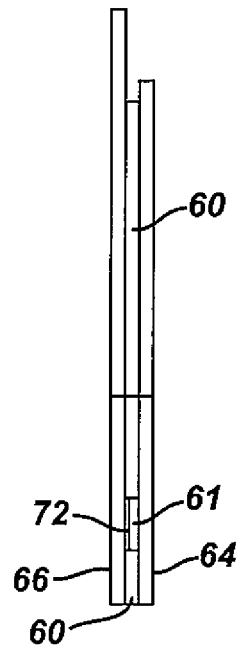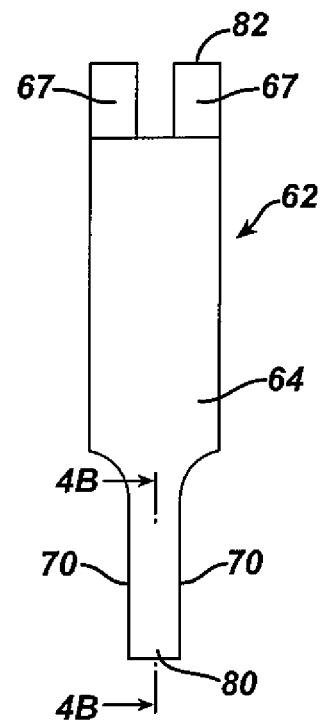
FIG. 2　　　FIG. 3　　　FIG. 4A
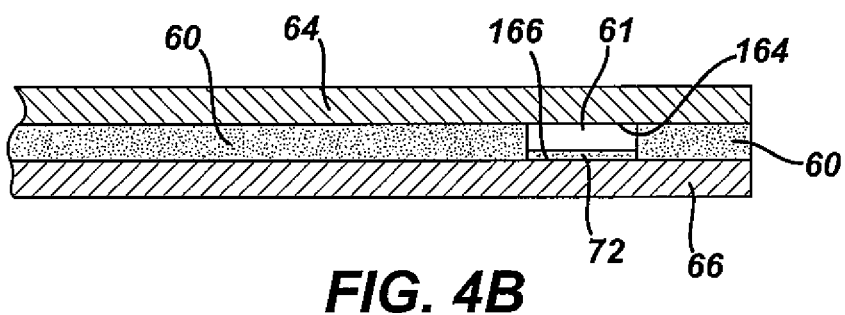
FIG. 4B

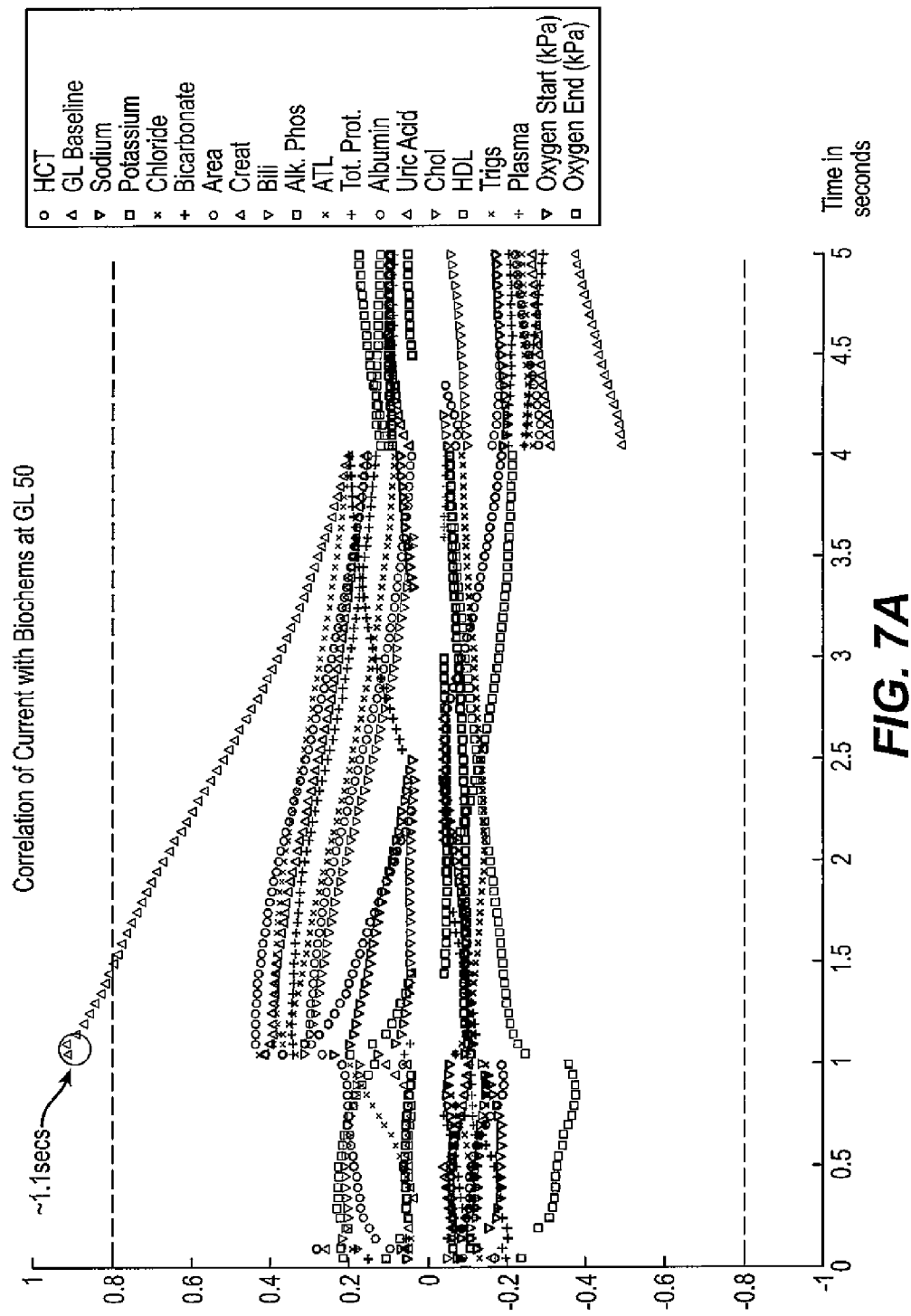

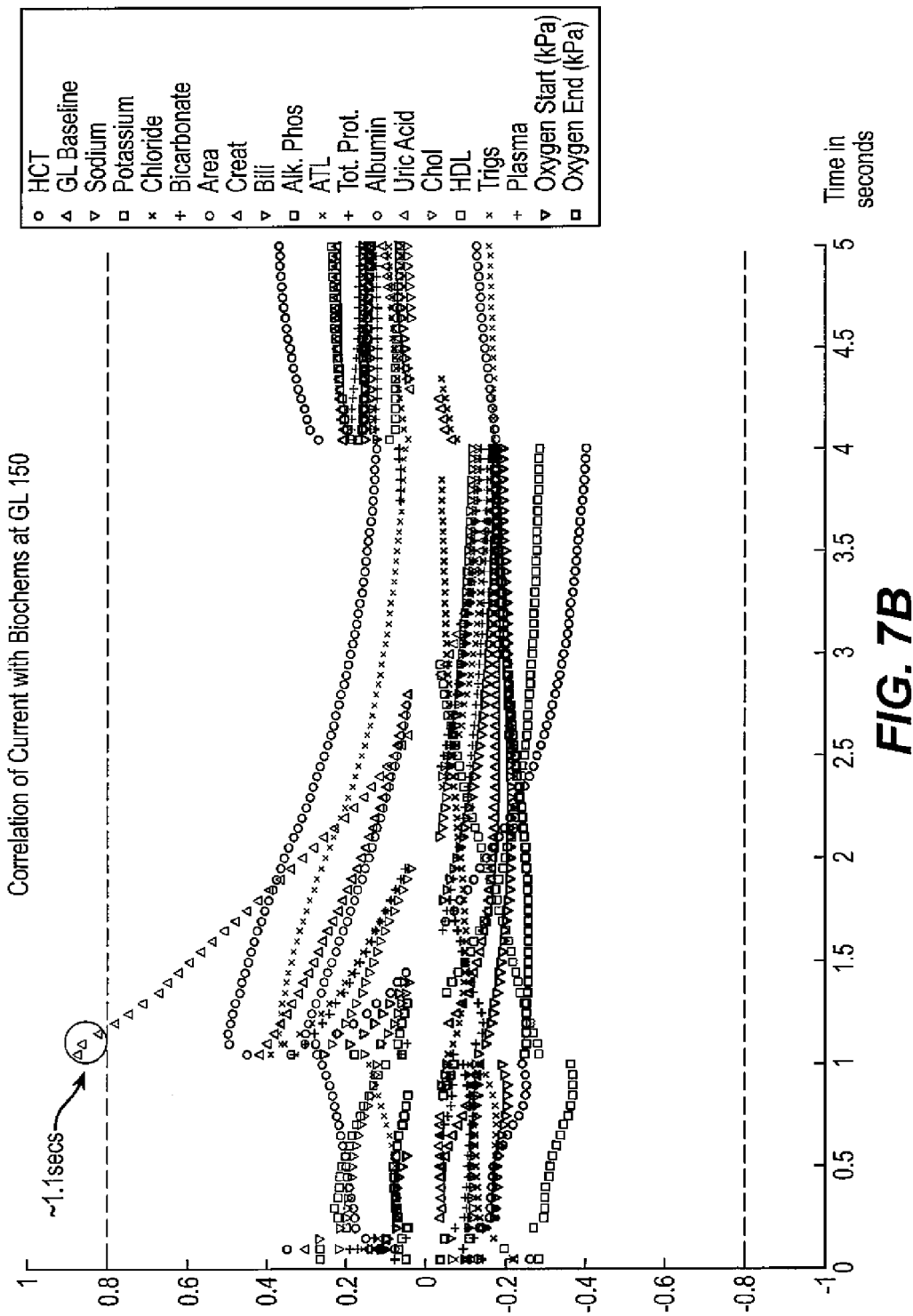

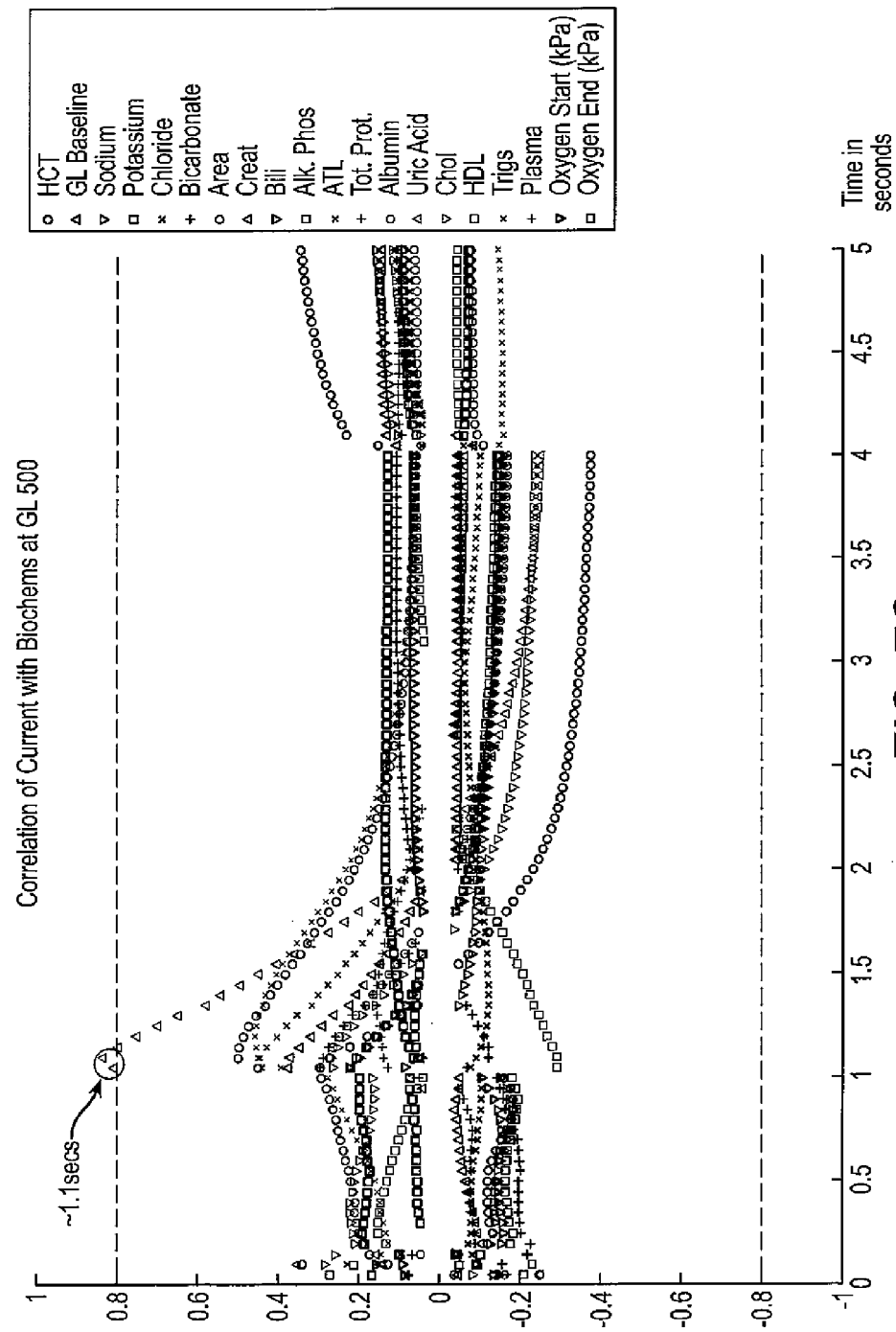

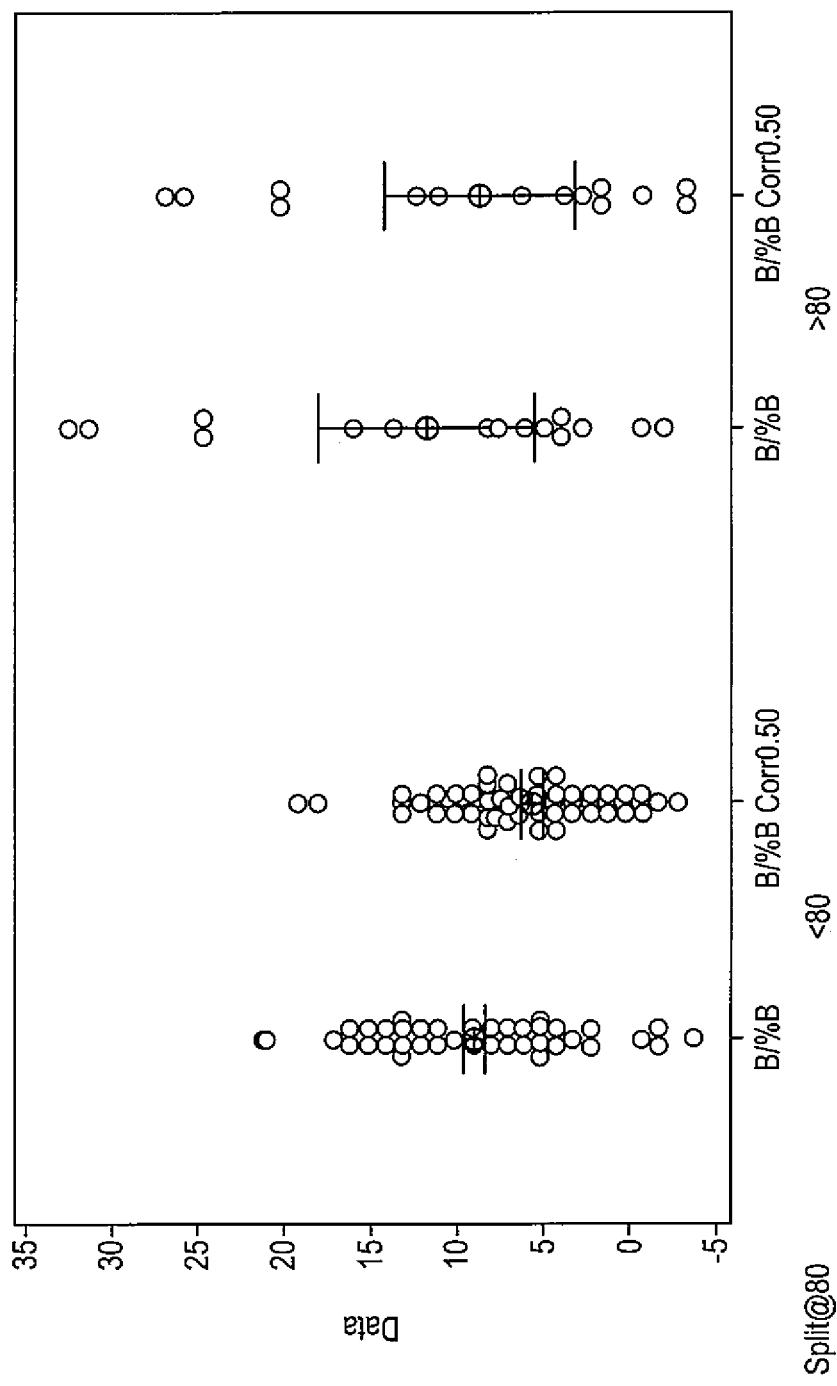

SYSTEM AND METHOD FOR DETERMINATION OF A CONCENTRATION OF AT LEAST ONE INTERFERING SUBSTANCE AND CORRECTION OF GLUCOSE CONCENTRATION BASED ON THE CONCENTRATION OF THE INTERFERING SUBSTANCE

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency or error. For example, interfering substances such as, for example, ascorbic acid, uric acid, creatine, urea and similar byproducts of metabolism may affect the results of the method.

SUMMARY OF THE DISCLOSURE

Applicant has discovered a technique to allow for greater precision and accuracy in analyte measurements despite varying levels of substances that are present in the sample and which may affect the ability of the glucose monitor to obtain an accurate measurement of the subject analyte in the sample. Briefly, applicant's technique involves estimating a glucose value of a fluid sample based on a measurement or sampling of the current output transient, categorizing the estimated glucose value into distinct categories of magnitudes, reviewing historical current output transient data to determine if the estimated glucose value from the estimating step could have a high correlation to at least one interfering substance at certain time points during a test sequence, estimating a concentration of such interfering substance at time points based on measured current at the certain time points and historical slopes and intercepts from regression analysis of historical current transient based on historical concentration of the interfering substance at such certain time points, correcting the current transient at such time points based on: (a) the measured current at the certain time points, (b) the historical slopes of current transient output for historical concentration of the interfering substance, (c) historical mean concentration of the interfering substance; and (d) estimated concentration of the interfering substance at the certain time points. The at least one interfering substance can be uric acid.

In another aspect, a method of determining an interferent corrected glucose concentration from a fluid sample with a glucose monitor and a biosensor is provided. This aspect can be achieved by first ascertaining historical data relating to interferent in physiological fluid samples by:

(I) determining a historical mean value for interferent including various standards of deviations from a plurality of physiological fluid samples measured separately by a referential interferent sensor at various glucose concentrations; storing the historical mean value of interferent in the plurality of physiological fluid samples; measuring current output transient of each of the plurality of the physiological fluid samples with respect to time points during a test sequence; and obtaining historical regression of slopes and intercepts, along with coefficients of determination of current output transient at corresponding time points with respect to a test interval for each sample of the plurality of samples; and retaining as historical data for each time point of the current transient of each of the physiological samples, the following parameters from regression analyses as a function of the interferent concentration at each specific glucose concentration: (a) regression slope, (b) regression intercept, and (c) coefficient of determination associated with the regression slope and regression intercept;

(II) depositing a physiological fluid sample in a test chamber of the biosensor to start a test sequence; applying a plurality of potential to electrodes disposed in the test chamber of the biosensor over a time interval of the test sequence; measuring a current output transient over a plurality of time points during the time interval of the test sequence to provide a measured current output transient for each of the plurality of time points; estimating a glucose value of a fluid sample from the measured current output transient of the measuring step; categorizing the estimated glucose value into one of plural distinct categories of glucose magnitudes; estimating a plurality of interferent values at specific time points based on: (a) the measured current output transient; and (b) historical slopes and historical intercepts of current transient output for historical interferent values that have been collected in the one category of glucose magnitudes; determining an estimated mean interferent value from the plurality of estimated interferent values of the estimating step; correcting the measured current output transient based on: (a) the measured current output transient at the specific time points during the test sequence, (b) the historical slope at the specific time points during the test sequence from historical data, and (c) historical mean interferent value and (d) estimated mean interferent value of the estimating step; and calculating a glucose concentration corrected for the presence of interferent based on the measured current output transient that includes the corrected current output transient at the specific time points from the correcting step.

In yet another aspect, a method of determining glucose concentration corrected for presence of interferent from a fluid sample with a glucose monitor and a biosensor is provided. The method can be achieved by: depositing a physiological fluid sample in a test chamber of the biosensor to start a test sequence; applying a plurality of potential to electrodes disposed in the test chamber of the biosensor over a time interval of the test sequence; measuring a current output transient over a plurality of time points during the time interval of the test sequence to provide a measured current output transient for each of the plurality of time points; estimating a glucose value of a fluid sample from the measured current output transient of the measuring step; categorizing the estimated glucose value into one of plural distinct categories of glucose magnitudes; estimating a plurality of interferent values at specific time points based on: (a) the measured current output transient; and (b) historical slopes and historical intercepts of current transient output for historical interferent values that have been collected in the one category of glucose magnitudes; determining an estimated mean interferent value from the plurality of estimated interferent values from the estimating step; correcting the measured current output transient based on a function of: (a) the measured current output transient at the specific time points during the test sequence, (b) the historical slope at the specific time points during the test sequence from historical data, and (c) a historical mean interferent value from historical data and (d) estimated mean interferent value of the estimating step; and calculating a glucose concentration corrected for the presence of interferent based on the measured current output transient that includes the corrected current output transient at the specific time points during the test sequence from the correcting step.

In yet a further aspect, a method of determining an interferent concentration from a fluid sample with a glucose monitor and a biosensor is provided. The method can be achieved by: depositing a physiological fluid sample in a test chamber of the biosensor to start a test sequence; applying a plurality of potential to electrodes disposed in the test chamber of the biosensor over a time interval of the test sequence; measuring a current output transient over a plurality of time points during the time interval of the test sequence to provide a measured current output transient for each of the plurality of time points; estimating a glucose value of a fluid sample from the measured current output transient of the measuring step; categorizing the estimated glucose value into one of plural distinct categories of glucose magnitudes; estimating a plurality of interferent values at specific time points based on: (a) the measured current output transient; and (b) historical slopes and historical intercepts of current transient output for historical interferent values that have been collected in the one category of glucose magnitudes; determining an estimated mean interferent value from the plurality of estimated interferent values from the estimating step.

In each of the above aspects, each of the following features may be combined with the above aspects by itself or in combination with other features provided herein. For example, the method may further include capping or limiting the estimated interferent value so that the estimated mean interferent value is within ±3 standard deviations of historical mean value of interferent concentrations; evaluating whether a historical coefficient of determination (from regression analysis over historical interferent values) at each of the plurality of time points that have been collected in a test sequence—for the one category of glucose magnitudes—is greater than a predetermined r-squared value; if the evaluating step is true, applying a correction to the current output transient for each of the plurality of time points that has a historical coefficient of determination greater than the predetermined r-squared value; or if the evaluating step is false then selecting another time point and returning to the evaluating step; the estimating of the interferent is performed with an equation of the form:

$$EstimatedInterferent(GL_{Group}, t) = \frac{Current(GL_{Group}, t) - Intercept(GL_{Group}, t)}{Slope(GL_{Group}, t)}$$

where EstimatedInterferent ($GL_{Group}$, t) is determined for each glucose categorization group and time points; Current ($GL_{Group}$, t) is the measured and uncorrected current output at the specified time point "t"; Intercept($GL_{Group}$, t) is obtained from historical data, including historical uncorrected current transients and historical interferent measurements at the specified time point "t"; Slope($GL_{Group}$, t) is obtained from historical data, including historical uncorrected current transients and historical interferent measurements at the specified time point "t"; and t includes any time point during the test sequence from about 0 second to about 5 seconds from a start of current output transient in the test sequence. Alternatively, the method may further include estimating an average interferent value based on all of the estimated interferent values at each of the time points for t, the estimating of the glucose concentration is obtained with an equation of the form:

$$G_{est} = \left(\frac{|i_r|}{|i_l|}\right)^p (a|i_{2CORR}| - zgr);$$

where: $G_{est}$ is the estimated glucose concentration:

$$i_r = \sum_{t=4.4}^{t=5} i(t);$$

$$i_l = \sum_{t=1.4}^{t=4} i(t);$$

and $$i_{2CORR} = \left(\frac{|i_{\approx 4.1secs}| + b|i_{\approx 5secs}| - c|i_{\approx 1.1secs}|}{|i_{\approx 4.1secs}| + b|i_{\approx 5secs}|}\right) i_r;$$

a is approximately 0.192, b is approximately 0.68, c is approximately 2, p is approximately 0.52, and zgr is approximately 2; and the calculating of the glucose concentration is performed after completion of the determining step for all of the plurality of time points during the time interval and is performed with an equation of the form:

$$G_{corr} = \left(\frac{|i_{rcorr}|}{|i_{lcorr}|}\right)^p (a|i_{2CORR}| - zgr);$$

where: $G_{corr}$ is the interferent corrected glucose concentration, $i_{corr}$ is a summation of corrected current transients, $i_{lcorr}$ is a summation of corrected current transients, $i_{corr\sim t}$ is a corrected current transient at each of the specified time points "t"

$$i_{rcorr} = \sum_{t=4.4}^{t=5} i(t)$$

$$i_{lcorr} = \sum_{t=1.4}^{t=4} i(t);$$

and $$i_{2CORR} = \left(\frac{|i_{corr\approx 4.1secs}| + b|i_{corr\approx 5secs}| - c|i_{corr\approx 1.1secs}|}{|i_{corr\approx 4.1secs}| + b|i_{corr\approx 5secs}|}\right) i_{rcorr};$$

a is approximately 0.192, b is approximately 0.68, c is approximately 2, p is approximately 0.52, and zgr is approximately 2.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 2 is a bottom plan view of one embodiment of a test strip disclosed herein;

FIG. 3 is a side plan view of the test strip of FIG. 2;

FIG. 4A is a top plan view of the test strip of FIG. 3;

FIG. 4B is a partial side view of a proximal portion of the test strip of FIG. 4A;

FIG. 7A illustrates the Spearman Correlation for various interfering substances in fluid samples with low glucose concentration of about 50 mg/dL in relation to various time points during a test sequence from a start to completion in about 5 seconds for the exemplary biosensor described herein.

FIG. 7B illustrates the Spearman Correlation for various interfering substances in fluid samples with medium glucose concentration of about 150 mg/dL in relation to various time points during a test sequence from a start to completion in about 5 seconds for the exemplary biosensor described herein.

FIG. 7C illustrates the Spearman Correlation for various interfering substances in fluid samples with very high glucose concentration of about 500 mg/dL in relation to various time points during a test sequence from a start to completion in about 5 seconds for the exemplary biosensor described herein.

FIG. 10 is an individual value plot of bias and percent-bias with respect to YSI referential datum for uncorrected and corrected measurements in the fifth study, in which the "split@80" indicates a split on glucose (YSI) values: whether they are greater than or less than 80 mg/dL.

MODES FOR CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment. Further, the term "value" is intended to have the same meaning as "concentration" when they relate to an analyte or a constituent of a sample and "interferent" or "interfering substance" means a substance that affects the assaying of an analyte such as, for example, a substance that skews the measurements of glucose in a sample.

Figure 1A:
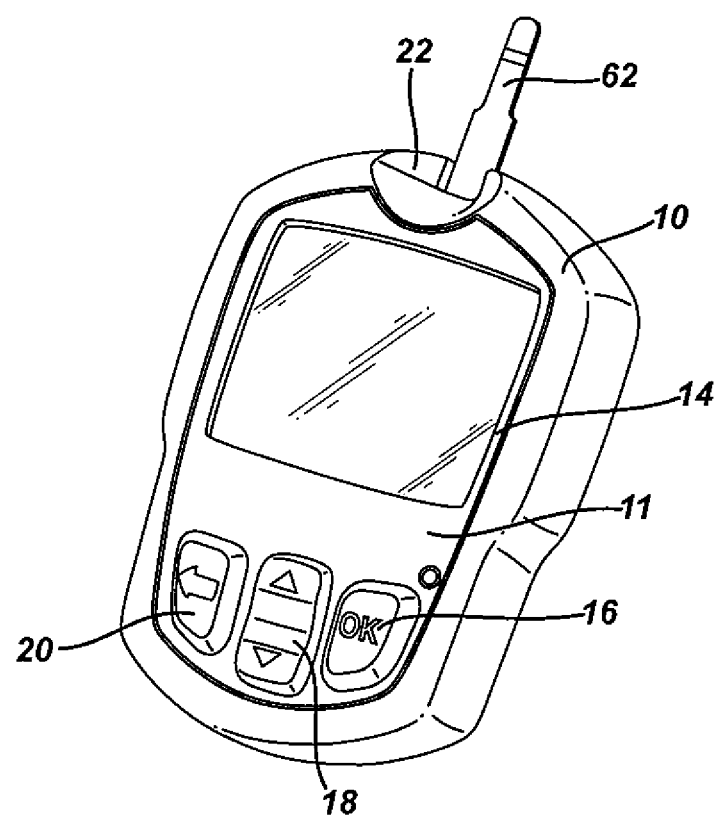
FIG. 1A illustrates a preferred blood glucose measurement system.

FIG. 1A illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1A, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 1B:
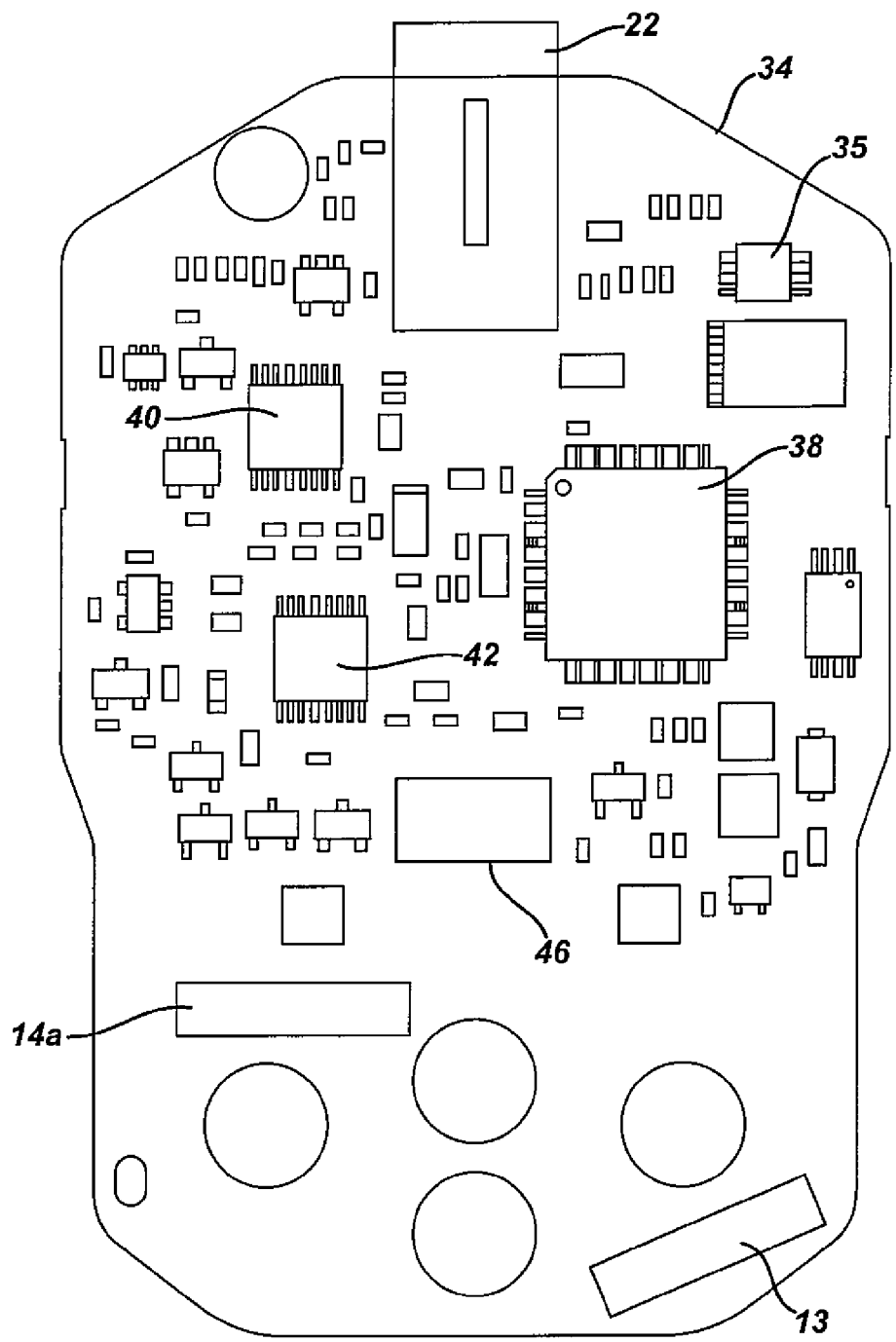
FIG. 1B illustrates the various components disposed in the meter of FIG. 1A.

FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14*a*, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14*a* may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

Figure 1C:
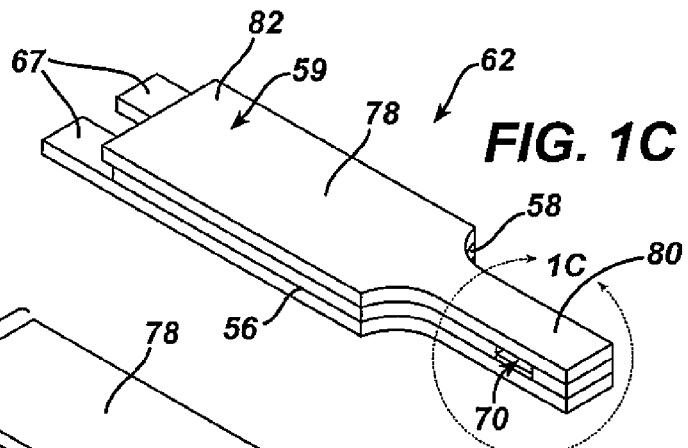
FIG. 1C illustrates a perspective view of an assembled test strip suitable for use in the system and methods disclosed herein.
Figure 1D:
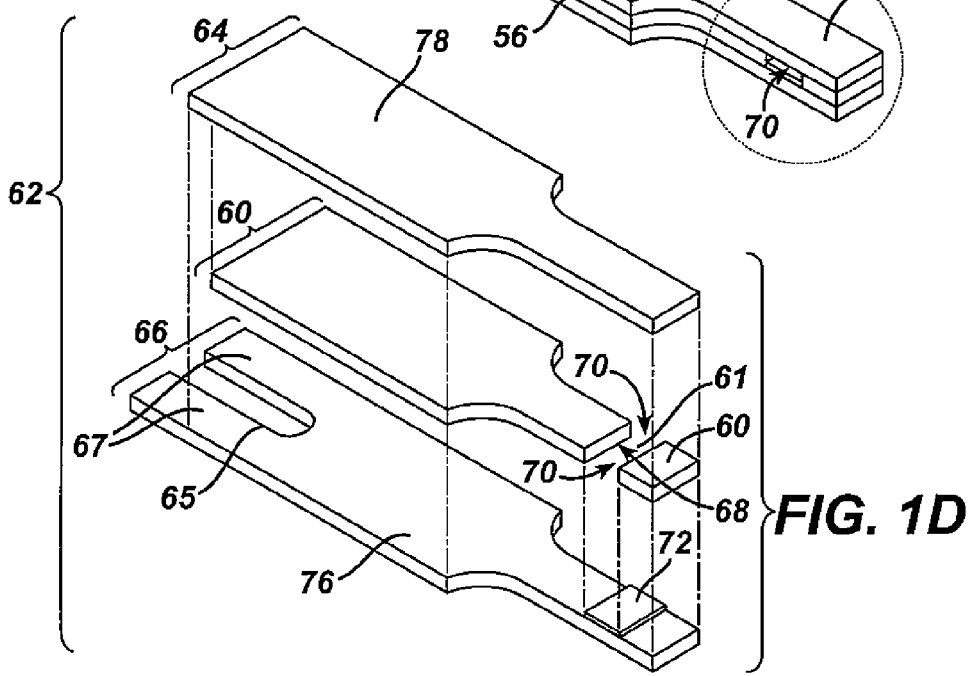
FIG. 1D illustrates an exploded perspective view of an unassembled test strip suitable for use in the system and methods disclosed herein.

FIGS. 1C-1E, 2, 3, and 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1C. As shown in FIG. 1D, the test strip 62 also includes a first electrode layer 66, a second electrode layer 64, and a spacer 60 sandwiched in between the two electrode layers 64 and 66. The first electrode layer 66 may include a first electrode 66, a first connection track 76, and a first contact pad 67, where the first connection track 76 electrically connects the first electrode to the first contact pad 67, as shown in FIGS. 1D and 4B. Note that the first electrode 66 is a portion of the first electrode layer 66 that is immediately underneath the reagent layer 72, as indicated by FIGS. 1D and 4B. Similarly, the second electrode layer 64 may include a second electrode 64, a second connection track 78, and a second contact pad 63, where the second connection track 78 electrically connects the second electrode 64 with the second contact pad 63, as shown in FIGS. 1D, 2, and 4B. Note that the second electrode 64 is a portion of the second electrode layer 64 that is above the reagent layer 72, as indicated by FIG. 4B.

Figure 1E:
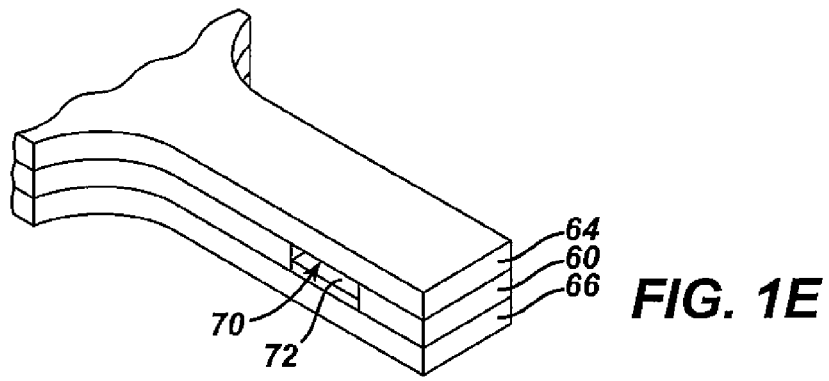
FIG. 1E illustrates an expanded perspective view of a proximal portion of the test strip suitable for use in the system and methods disclosed herein.

As shown, the sample-receiving chamber 61 is defined by the first electrode 66, the second electrode 64, and the spacer 60 near the distal end 80 of the test strip 62, as shown in FIGS. 1D and 4B. The first electrode 66 and the second electrode 64 may define the bottom and the top of sample-receiving chamber 61, respectively, as illustrated in FIG. 4B. A cutout area 68 of the spacer 60 may define the sidewalls of the sample-receiving chamber 61, as illustrated in FIG. 4B. In one aspect, the sample-receiving chamber 61 may include ports 70 that provide a sample inlet or a vent, as shown in FIGS. 1C to 1E. For example, one of the ports may allow a fluid sample to ingress and the other port may allow air to egress.

In an exemplary embodiment, the sample-receiving chamber 61 (or test cell or test chamber) may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 $cm^2$ to about 0.2 $cm^2$, about 0.02 $cm^2$ to about 0.15 $cm^2$, or, preferably, about 0.03 $cm^2$ to about 0.08 $cm^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at first electrode 66, may diffuse to second electrode 64 to become reduced, and subsequently diffuse back to first electrode 66 to become oxidized again. Those skilled in the art will appreciate that various such volumes, areas, or spacing of electrodes is within the spirit and scope of the present disclosure.

In one embodiment, the first electrode layer 66 and the second electrode layer 64 may be a conductive material formed from materials such as gold, palladium, carbon, silver, platinum, tin oxide, iridium, indium, or combinations thereof (e.g., indium doped tin oxide). In addition, the electrodes may be formed by disposing a conductive material onto an insulating sheet (not shown) by a sputtering, electroless plating, or a screen-printing process. In one exemplary embodiment, the first electrode layer 66 and the second electrode layer 64 may be made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, or the spacer 60 are within the spirit and scope of the present disclosure.

Either the first electrode 66 or the second electrode 64 may perform the function of a working electrode depending on the magnitude or polarity of the applied test voltage. The working electrode may measure a limiting test current that is proportional to the reduced mediator concentration. For example, if the current limiting species is a reduced mediator (e.g., ferrocyanide), then it may be oxidized at the first electrode 66 as long as the test voltage is sufficiently greater than the redox mediator potential with respect to the second electrode 64. In such a situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term "bulk solution" refers to a portion of the solution sufficiently far away from the working electrode where the reduced mediator is not located within a depletion zone. It should be noted that unless otherwise stated for test strip 62, all potentials applied by test meter 10 will hereinafter be stated with respect to second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into a sample-receiving chamber 61 via a port 70. In one aspect, the port 70 or the sample-receiving chamber 61 may be configured such that capillary action causes the fluid sample to fill the sample-receiving chamber 61. The first electrode 66 or second electrode 64 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode or the second electrode.

In the analysis of strip 62 above, reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by $GDH_{(ox)}$ and in the process converts $GDH_{(ox)}$ to $GDH_{(red)}$, as shown in the chemical transformation T.1 below. Note that $GDH_{(ox)}$ refers to the oxidized state of GDH, and $GDH_{(red)}$ refers to the reduced state of GDH.

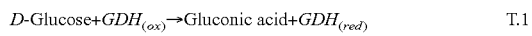

D-Glucose+$GDH_{(ox)}$→Gluconic acid+$GDH_{(red)}$   T.1

Next, $GDH_{(red)}$ is regenerated back to its active oxidized state by ferricyanide (i.e. oxidized mediator or $Fe(CN)_6^{3-}$) as shown in chemical transformation T.2 below. In the process of regenerating $GDH_{(ox)}$, ferrocyanide (i.e. reduced mediator or $Fe(CN)_6^{4-}$) is generated from the reaction as shown in T.2:

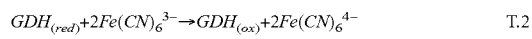

$GDH_{(red)}$+$2Fe(CN)_6^{3-}$→$GDH_{(ox)}$+$2Fe(CN)_6^{4-}$   T.2

Figure 5:
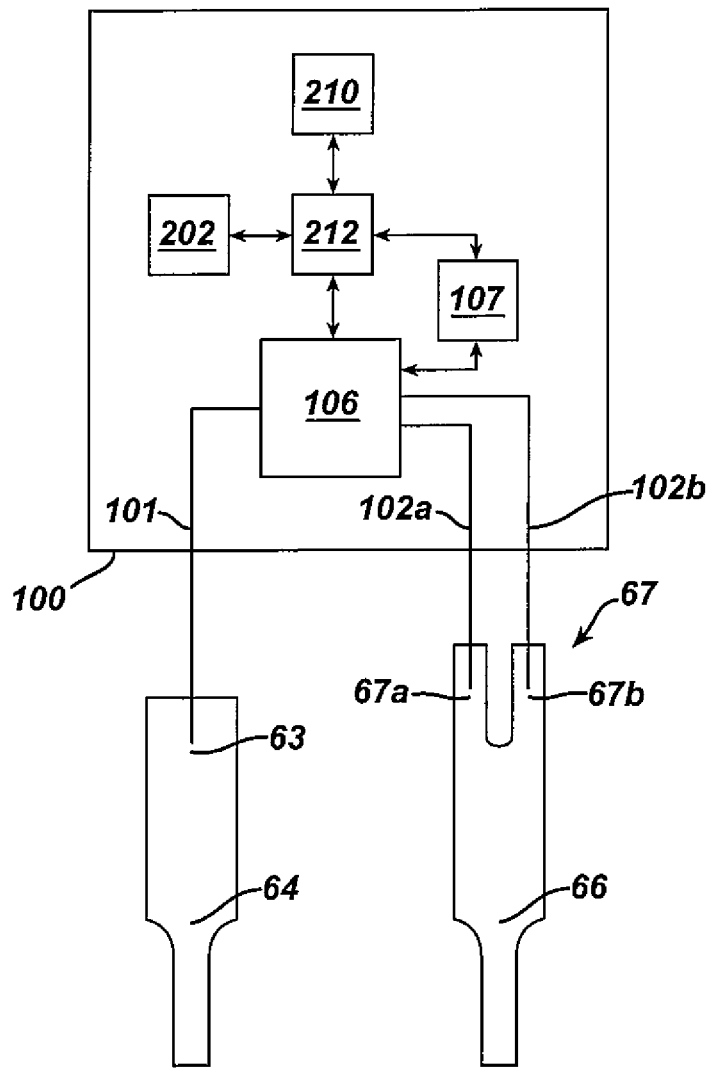
FIG. 5 is a simplified schematic showing a test meter electrically interfacing with portions of a test strip disclosed herein.

FIG. 5 provides a simplified schematic showing a test meter 100 interfacing with a first contact pad 67a, 67b and a second contact pad 63. The second contact pad 63 may be used to establish an electrical connection to the test meter through a U-shaped notch 65, as illustrated in FIG. 2. In one embodiment, the test meter 100 may include a second electrode connector 101, and a first electrode connectors (102a, 102b), a test voltage unit 106, a current measurement unit 107, a processor 212, a memory unit 210, and a visual display 202, as shown in FIG. 5. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 100 may measure the resistance or electrical continuity between the prongs 67a and 67b to determine whether the test strip 62 is electrically connected to the test meter 10. The electrodes 64 and 66 here can be utilized to detect physical characteristics of the sample using alternating signals. Alternatively, separate additional electrodes can be provided in the test chamber to allow for detection of the physical characteristics of the sample using alternating signals.

Figure 6A:
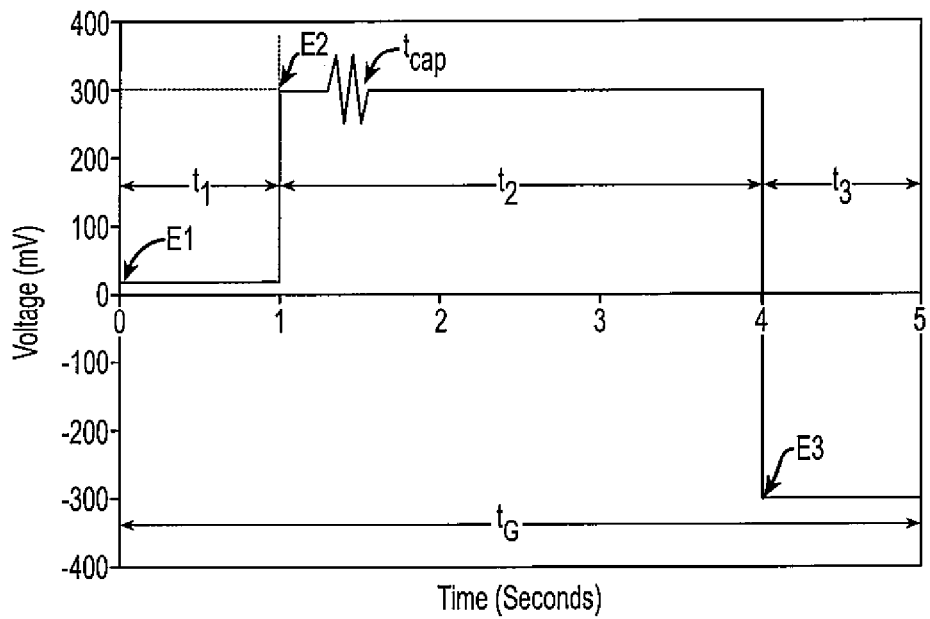
FIG. 6A shows an example of a tri-pulse potential waveform applied by the test meter of FIG. 5 to the working and counter electrodes for prescribed time intervals.

FIG. 6A is an exemplary chart of a plurality of test voltages or potentials applied to the test strip 62 for prescribed intervals. The plurality of test voltages may include a first test voltage E1 for a first time interval $t_1$, a second test voltage E2 for a second time interval $t_2$, and a third test voltage E3 for a third time interval $t_3$. The third voltage E3 may be different in the magnitude of the electromotive force, in polarity, or combinations of both with respect to the second test voltage E2. In the preferred embodiments, E3 may be of the same magnitude as E2 but opposite in polarity. A glucose test sequence interval $t_G$ represents an amount of time to perform the glucose test (but not necessarily all the calculations associated with the glucose test). Glucose test time interval $t_G$ may range from about 1.1 seconds to about 5 seconds. Further, as illustrated in FIG. 6A, the second test voltage E2 may include a direct (DC) test voltage component and a superimposed alternating (AC), or alternatively oscillating, test voltage component. The superimposed alternating or oscillating test voltage component may be applied for a time interval indicated by $t_{cap}$.

The plurality of test current values measured during any of the time intervals may be performed at a sampling frequency ranging from about 1 measurement per microsecond to about one measurement per 100 milliseconds and preferably at about every 50 milliseconds. While an embodiment using three test voltages in a serial manner is described, the glucose test may include different numbers of open-circuit and test voltages. For example, as an alternative embodiment, the glucose test could include an open-circuit for a first time interval, a second test voltage for a second time interval, and a third test voltage for a third time interval. It should be noted that the reference to "first," "second," and "third" are chosen for convenience and do not necessarily reflect the order in which the test voltages are applied. For instance, an embodiment may have a potential waveform where the third test voltage may be applied before the application of the first and second test voltage.

In this exemplary system, the process for the system may apply a first test voltage E1 (e.g., approximately 20 mV in FIG. 6A) between first electrode 66 and second electrode 64 for a first time interval $t_1$ (e.g., 1 second in FIG. 6A). The first time interval $t_1$ may range from about 0.1 seconds to about 3 seconds and preferably range from about 0.2 seconds to about 2 seconds, and most preferably range from about 0.3 seconds to about 1.1 seconds.

Figure 6B:
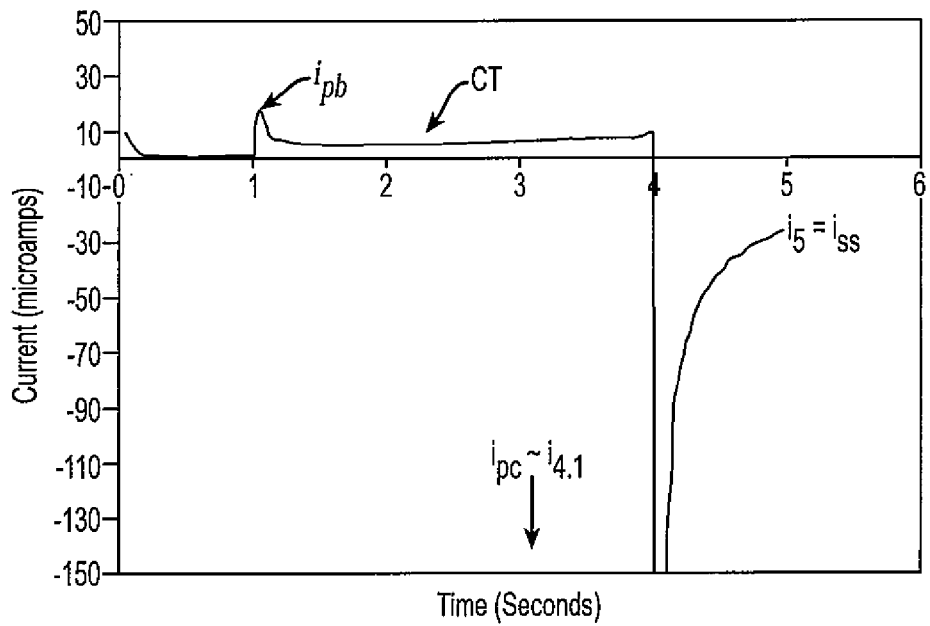
FIG. 6B shows a current transient CT generated by a physiological sample.

The first time interval $t_1$ may be sufficiently long so that the sample-receiving or test chamber 61 (defined partly by first wall 164 and second wall 166) may fully fill with sample and also so that the reagent layer 72 may at least partially dissolve or solvate. In one aspect, the first test voltage E1 may be a value relatively close to the redox potential of the mediator so that a relatively small amount of a reduction or oxidation current is measured. FIG. 6B shows that a relatively small amount of current is observed during the first time interval $t_1$ compared to the second and third time intervals $t_2$ and $t_3$. For example, when using ferricyanide or ferrocyanide as the mediator, the first test voltage E1 in FIG. 6A may range from about 1 millivolts ("mV") to about 100 mV, preferably range from about 5 mV to about 50 mV, and most preferably range from about 10 mV to about 30 mV. Although the applied voltages are given as positive values in the preferred embodiments, the same voltages in the negative domain could also be utilized to accomplish the intended purpose of the claimed invention.

Referring back to FIG. 6A, after applying the first test voltage E1, the test meter 10 applies a second test voltage E2 between first electrode 66 and second electrode 64 (e.g., approximately 300 mVolts in FIG. 6A), for a second time interval $t_2$ (e.g., about 3 seconds in FIG. 6A). The second test voltage E2 may be a value different than the first test voltage E1 and may be sufficiently negative of the mediator redox potential so that a limiting oxidation current is measured at the second electrode 64. For example, when using ferricyanide or ferrocyanide as the mediator, the second test voltage E2 may range from about zero mV to about 600 mV, preferably range from about 100 mV to about 600 mV, and more preferably is about 300 mV.

The second time interval $t_2$ should be sufficiently long so that the rate of generation of reduced mediator (e.g., ferrocyanide) may be monitored based on the magnitude of a limiting oxidation current. Reduced mediator is generated by enzymatic reactions with the reagent layer 72. During the second time interval $t_2$, a limiting amount of reduced mediator is oxidized at second electrode 64 and a non-limiting amount of oxidized mediator is reduced at first electrode 66 to form a concentration gradient between first electrode 66 and second electrode 64.

In an exemplary embodiment, the second time interval $t_2$ should also be sufficiently long so that a sufficient amount of ferricyanide may be diffused to the second electrode 64 or diffused from the reagent on the first electrode. A sufficient amount of ferricyanide is required at the second electrode 64 so that a limiting current may be measured for oxidizing ferrocyanide at the first electrode 66 during the third test voltage E3. The second time interval $t_2$ may be less than about 60 seconds, and preferably may range from about 1.1 seconds to about 10 seconds, and more preferably range from about 2 seconds to about 5 seconds. Likewise, the time interval indicated as $t_{cap}$ in FIG. 6A may also last over a range of times, but in one exemplary embodiment $t_{cap}$ has a duration of about 20 milliseconds. In one exemplary embodiment, the superimposed alternating test voltage component is applied after about 0.3 seconds to about 0.4 seconds after the application of the second test voltage E2, and induces a sine wave having a frequency of about 109 Hz with an amplitude of about +/−50 mV.

FIG. 6B shows a relatively small peak $i_{pb}$ after the beginning of the second time interval $t_2$ followed by a gradual increase of an absolute value of an oxidation current during the second time interval $t_2$. The small peak $i_{pb}$ occurs due oxidation of endogenous or exogenous reducing agents (e.g., uric acid) after a transition from first voltage E1 to second voltage E2. Thereafter, there is a gradual absolute decrease in oxidation current after the small peak $i_{pb}$ is caused by the generation of ferrocyanide by reagent layer 72, which then diffuses to second electrode 64.

As part of step 904 after application of the second test voltage E2, the test meter 10 applies a third test voltage E3 between the first electrode 66 and the second electrode 64 (e.g., about −300 mVolts in FIG. 6A) for a third time interval $t_3$ (e.g., 1 second in FIG. 6A). The third test voltage E3 may be a value sufficiently positive of the mediator redox potential so that a limiting oxidation current is measured at the first electrode 66. For example, when using ferricyanide or ferrocyanide as the mediator, the third test voltage E3 may range from about zero mV to about −600 mV, preferably range from about −100 mV to about −600 mV, and more preferably is about −300 mV.

The third time interval $t_3$ may be sufficiently long to monitor the diffusion of reduced mediator (e.g., ferrocyanide) near the first electrode 66 based on the magnitude of the oxidation current. During the third time interval $t_3$, a limiting amount of reduced mediator is oxidized at first electrode 66 and a non-limiting amount of oxidized mediator is reduced at the second electrode 64. The third time interval $t_3$ may range from about 0.1 seconds to about 5 seconds and preferably range from about 0.3 seconds to about 3 seconds, and more preferably range from about 0.5 seconds to about 2 seconds.

FIG. 6B shows a relatively large peak $i_{pc}$ at the beginning of the third time interval $t_3$ followed by a decrease to a steady-state current $i_{ss}$ value. In one embodiment, the second test voltage E2 may have a first polarity and the third test voltage E3 may have a second polarity that is opposite to the first polarity. In another embodiment, the second test voltage E2 may be sufficiently negative of the mediator redox potential and the third test voltage E3 may be sufficiently positive of the mediator redox potential. The third test voltage E3 may be applied immediately after the second test voltage E2. However, one skilled in the art will appreciate that the magnitude and polarity of the second and third test voltages may be chosen depending on the manner in which analyte concentration is determined.

Referring to FIG. 6B, the system at step 906 also measure a second current output of the current transient from the electrodes after the changing from the second voltage to the third voltage and then the system proceeds by estimating a current that approximates a steady state current output of the current transient after the third voltage is maintained at the electrodes.

The system calculates a blood glucose concentration based on the first, second and third current outputs of the current transient and the analyte calculation coefficients. The glucose concentration G may be calculated using a glucose algorithm as shown in Equation 1:

$$G = \left(\frac{|i_2|}{|i_3|}\right)^p (a \times i_1 - z) \qquad \text{Eq. 1}$$

Where
$i_1$ is a first test current value,
$i_2$ is a second test current value,
$i_3$ is a third test current value, and
the terms a, p, and z can be empirically derived analyte calculation coefficients.

The first test current value $i_1$ and the second test current value $i_2$ can each be defined by an average or summation of one or more predetermined test current values that occur during the third time interval $t_3$. The term $i_2$ is a second current value that is based on a fourth current value $i_4$, a fifth current value $i_5$, and a sixth current value $i_6$ measured during a third time interval. The third test current value $i_3$ can be defined by an average or summation of one or more predetermined test current values that occur during the second time interval $t_2$. One skilled in the art will appreciate that names "first," "second," and "third" are chosen for convenience and do not necessarily reflect the order in which the current values are calculated. A derivation of Eq. 1 can be found in U.S. Pat. No. 7,749,371, patented Jul. 6, 2010, which was filed on 30 Sep., 2005 and entitled "Method and Apparatus for Rapid Electrochemical Analysis," which is hereby incorporated by reference in its entirety into this application and attached hereto as part of the Appendix.

Referring now to FIGS. 6A and 6B, the peak current (FIG. 6B) observed at the end of $t_1$ and the beginning of the second test potential time interval $t_2$ (FIG. 6A) may be denoted as $i_{pb}$, and the peak current exhibited at the start of the third test potential time interval $t_3$ (FIG. 6A) may be denoted as $i_{pc}$. Equation 2 describes a relationship between the first current transient CT and second current transient CT when a test strip 62 is tested with a sample containing an interferent and no glucose.

$$i_{pc} - 2i_{pb} = -i_{ss} \qquad \text{Eq. 2}$$

In the case where there is no glucose in the sample, it is believed that the reagent layer 72 does not generate substantial amount of reduced mediator. Therefore, the current transients would reflect only the oxidation of interferents. At the early time scale regime of around 1.0 seconds, it is assumed that reagent layer 72 does not generate a significant amount of reduced mediator because of the glucose reaction. Further, it is assumed that the reduced mediator which is generated will mostly remain near first electrode 66, where reagent layer 72 was initially deposited, and not significantly diffuse to second electrode 64. Therefore, the magnitude of $i_{pb}$ is predominantly ascribed to interferent oxidation at second electrode 64 which is a direct interferent current.

At a duration after the third voltage E3 has been provided to the strip (e.g., about −300 mV) at around 4.1 seconds, reagent layer 72 does generate a significant amount of reduced mediator at first electrode 66 in the presence of glucose because of the glucose reaction. A significant amount of reduced mediator can also be generated because of a possible oxidation of an interferent with the oxidized mediator. As mentioned earlier, interferent that reduces oxidized mediator contributes to a current which may be referred to as an indirect current. In addition, interferents can also be oxidized directly at first electrode 66 which may be referred to as a direct current. For the situation in which the mediator can be oxidized at the working electrode, it may be assumed that the sum of the direct oxidation and indirect oxidation is approximately equal to a direct oxidation current that would have been measured if there was no oxidized mediator disposed on the working electrode. In summary, the magnitude of the $i_{pc}$ is ascribed to both indirect and direct interferent oxidation, and the glucose reaction at the first electrode 66. Because it has been determined that $i_{pb}$ is controlled mainly by interferents, $i_{pc}$ can be used with $i_{pb}$ together to determine a correction factor. For example, as shown below $i_{pb}$ can be used with $i_{pc}$ in a mathematical function to determine a corrected current $i_{2(Corr)}$ which is proportional to glucose and less sensitive to interferents:

$$i_{2CORR} = i_2 \left[ \frac{|i_{pc}| - |2i_{pb}| + |i_{ss}|}{|i_{pc}| + |i_{ss}|} \right] \qquad \text{Eq. 3}$$

In exemplary step 612, $i_{pb}$ is measured after the start of the second test potential time interval $t_2$ and $i_{pc}$ is measured at the start of the third test potential time interval $t_3$. Applicants note that $i_{pc}$ may be the test current value at about 4.1 seconds, and $i_{pb}$ may be the test current value at about 1.1 second, based on the test voltage and test current waveforms in FIGS. 6A and 6B.

Eq. 3 was empirically derived to calculate a current $i_{2(Corr)}$ which is proportional to glucose and has a relative fraction of current removed that is ascribed to interferents. The term $i_{ss}$ was added to both the numerator and denominator to allow the numerator to approach zero when no glucose is present. Determination of the steady-state current $i_{ss}$ following application of the second electric potential is detailed in co-pending patent application Ser. No. 11/278,341, which is incorporated by reference into this application herein and attached hereto as part of the Appendix. Some examples of methods for calculating $i_{ss}$ can be found in U.S. Pat. Nos. 5,942,102 and 6,413,410, each of which is hereby incorporated by reference in its entirety and attached hereto as part of the Appendix.

In the calculation of glucose, $i_{ss}$ is estimated by multiplying the test current value at about 5 seconds with a constant $K_8$ (e.g., 0.678). Thus, $i_{ss}$ can be approximated as i (5 secs.)$\times K_8$. The term $K_8$ can be estimated using Equation 4 where the number 0.975 is about the time in seconds after the third test voltage E3 is applied that corresponds to the current at approximately 5 seconds for the particular embodiment of the strip 62, which, assuming a linear variation over the time between about 0.95 seconds and 1 second, is the average current between 0.95 and 1 second, the term D is assumed to be about $5 \times 10^{-6}$ cm$^2$/sec as a typical diffusion coefficient in blood, and the term L is assumed to be about 0.0095 cm, which represents the height of the spacer 60:

$$i_{ss} = \frac{i(5)}{1 + 4\exp\left(\frac{-4\pi^2 D \times 0.975}{L^2}\right)} \qquad \text{Eq. 4}$$

Hence, a first blood glucose concentration G can be determined by Equation 5 that utilizes current $i_{2Corr}$ (which is proportional to glucose and has a relative fraction of current removed that is ascribed to interferents):

$$G = \left(\frac{|i_r|}{|i_l|}\right)^p (a|i_{2CORR}| - zgr); \qquad \text{Eq. 5}$$

$$\text{where: } i_r = \sum_{t=4.4}^{t=5} i(t);$$

$$i_l = \sum_{t=1.4}^{t=4} i(t);$$

$$i_{2CORR} = \left(\frac{|i_{pc}| + b|i_{ss}| - c|i_{pb}|}{|i_{pc}| + b|i_{ss}|}\right) i_r; \qquad \text{Eq. 5.1}$$

and

Where a, b, c, p, and zgr are glucose calculation coefficients.

Although the applied voltages are given as positive values in the preferred embodiments, the same voltages in the negative domain could also be utilized to accomplish the intended purpose of the claimed invention.

In this exemplary embodiment, $i_{pb}$ is the current measured at approximately 1.1 second; $i_{pc}$ is current measured from the electrodes of the strip 62 at approximately 4.1 seconds; $i_{ss}$ is the current measured at approximately 5 seconds. For ease of notation, Eq. 5.1 for this known glucose concentration calculation, can be represented in the following notation as Equation 5.2:

$$i_{2CORR} = \left( \frac{|i_{\cong 4.1secs}| + b|i_{\cong 5secs}| - c|i \cong_{1.1secs}|}{|i_{\cong 4.1secs}| + b|i_{\cong 5secs}|} \right) i_r \quad \text{Eq. 5.2}$$

In some embodiments of the systems and methods of the present invention, a blood temperature correction can be applied to the test current values to provide an analyte concentration with an improved accuracy because of a reduced effect from temperature. A method for calculating a temperature corrected analyte concentration can include measuring a temperature value and calculating a temperature correction value $C_T$. The temperature correction value $C_T$ can be based on a temperature value and an analyte concentration, e.g., a glucose concentration. Accordingly, the temperature correction value $C_T$ can then be used to correct the analyte concentration for temperature. The temperature can be measured using a thermistor or other temperature reading device that is incorporated into a test meter, or by way of any number of other mechanisms or means. Subsequently, a determination can be performed to determine whether the temperature value T is greater than a first temperature threshold $T_1$. For example, the temperature threshold $T_1$ can be about 15° C. If the temperature value T is greater than 15° C., then a first temperature function can be applied to determine the temperature correction value $C_T$. If the temperature value T is not greater than 15° C., then a second temperature function can be applied to determine the temperature correction value $C_T$.

The first temperature function for calculating the temperature correction value $C_T$ can be in the form of Equation 5.3:

$$C_T = -K_9(T - T_{RT}) + K_{10}[G](T - T_{RT}) \quad \text{Eq. 5.3}$$

where $C_T$ is the correction value, $K_9$ is a ninth constant (e.g., 0.59), T is a temperature value, $T_{RT}$ is a room temperature value (e.g., 22° C.), $K_{10}$ is a tenth constant (e.g., 0.00004), and [G] is the glucose concentration. When T is about equal to $T_{RT}$, $C_T$ is about zero. In some instances, the first temperature function can be configured to have essentially no correction at room temperature such that variation can be reduced under routine ambient conditions. The second temperature function for calculating the second correction value $C_T$ can be in the form of Equation 5.4:

$$C_T = -K_{11}(T - T_{RT}) - K_{12}[G]T - T_{RT}) - K_{13}[G](T - T_1) + K_{14} [G](T - T_1) \quad \text{Eq. 5.4}$$

where $C_T$ is the correction value, $K_{11}$ is an eleventh constant (e.g., 0.59), T is a temperature value, $T_{RT}$ is a room temperature value, $K_{12}$ is a twelfth constant (e.g., 0.00004), [G] is a glucose concentration, $K_{13}$ is a thirteenth constant (e.g., 1.2), $T_1$ is a first temperature threshold, and $K_{14}$ is a fourteenth constant (e.g., 0.005).

After $C_T$ is calculated using Equation 5.4, a couple of truncation functions can be performed to ensure that $C_T$ is constrained to a pre-determined range, thereby mitigating the risk of an outlier. In one embodiment $C_T$ can be limited to have a range of −10 to +10. For example, a determination can be performed to determine whether $C_T$ is greater than 10. If $C_T$ is greater than 10, then $C_T$ is set to 10. If $C_T$ is not greater than 10, then a determination is performed to determine whether $C_T$ is less than −10. $C_T$ can be set to −10 if $C_T$ is less than −10. If $C_T$ is a value already in between −10 and +10, then there generally is no need for truncation.

Once $C_T$ is determined, a temperature corrected glucose concentration can be calculated. For example, a determination can be performed to determine whether the glucose concentration uncorrected for temperature (e.g., [G]) is less than 100 mg/dL. If [G] is less than 100 mg/dL, then an Equation 5.5 can be used to calculate the temperature corrected glucose concentration $G_T$ by adding the correction value $C_T$ to the glucose concentration [G]:

$$G_T = [G] + C_T. \quad \text{Eq. 5.5}$$

If [G] is not less than 100 mg/dL, then an Equation 5.6 can be used to calculate the temperature corrected glucose concentration $G_T$ by dividing $C_T$ by one hundred, adding one; and then multiplying by the glucose concentration [G]:

$$G_T = [G]/[1 + 0.01 \times C_T]. \quad \text{Eq. 5.6}$$

Once a glucose concentration is determined that has been corrected for the effects of temperature, the glucose concentration can be output, e.g., to a display.

During experimentation with various interferents that are present in physiological fluid sample (with the subject biosensor 62 described earlier), applicant has discovered that there is a strong correlation between interferent and the output current transient. In particular, as shown in FIGS. 7A, 7B, and 7C, the Spearman correlation is very noticeable for an interferent such as, for example, uric acid, at approximately 1 second (denoted by arrow and circle in the figures) into the output current transient of FIG. 6B. For example, at glucose concentration of about 50 mg/dL of FIG. 7A, the correlation is approximately 0.9; at glucose concentration of about 150 mg/dL of FIG. 7B, the correlation is greater than 0.8; and at glucose concentration of about 500 mg/dL of FIG. 7C, the correlation is still about 0.8.

Applicant notes that the correlation is very good around the time point of about 1 second (e.g., 1.05-1.5 seconds with intervals of 10 milliseconds between this range) for this type of biosensor. As the current transient at 1.1 second affects $i_{2CORR}$ of Equation 5.2 above, it is believed that this might be the reason that the exemplary biosensor appears to be sensitive to the interfering effects of a particular interferent of interest, uric acid.

Figure 7D:
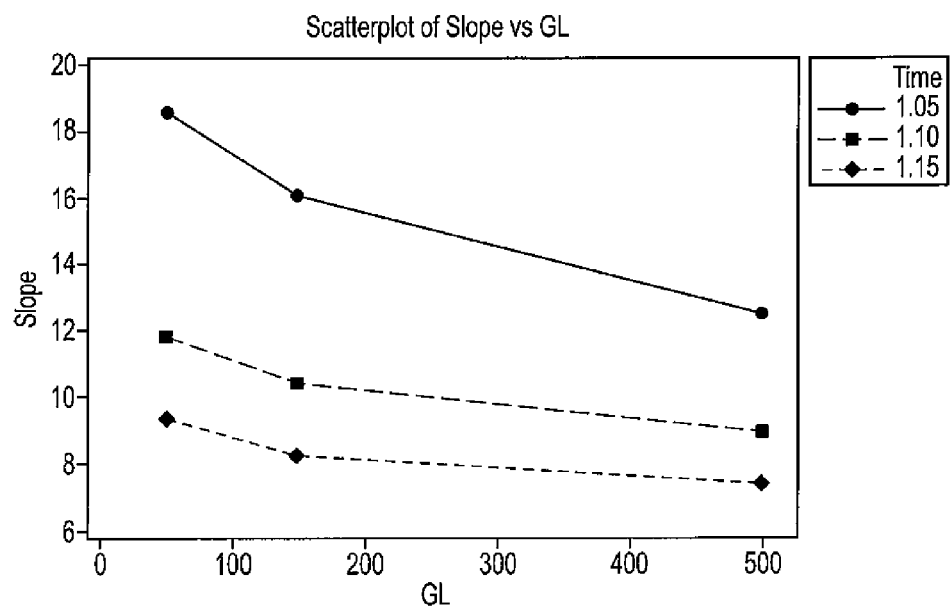
FIG. 7D illustrates a scatterplot of respective slopes resulting from linear regression analysis of current transient of samples having low, medium and high glucose at certain time points (e.g., at 1.05 secs; 1.1 secs; 1.15 secs) against uric concentration in such samples.
Figure 7E:
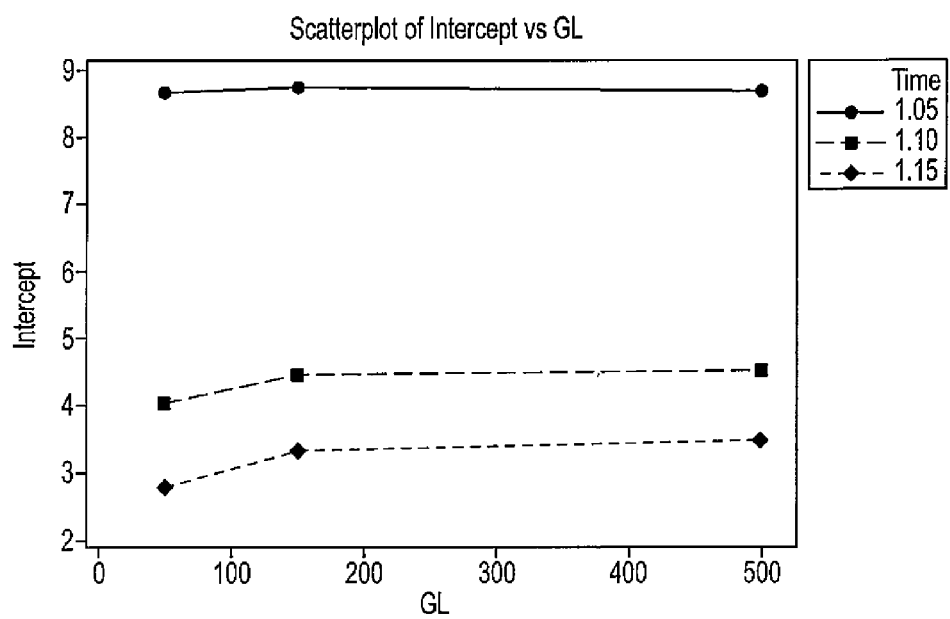
FIG. 7E illustrates a scatterplot of respective intercepts resulting from linear regression analysis of current transient of samples having low, medium and high glucose at certain time points (e.g., at 1.05 secs; 1.1 secs; 1.15 secs) against the exemplary interferent concentration (in the form of uric-acid) in such samples.

Applicant has also discovered that the "slopes" and "intercepts" of the linear regression of the current output transient are also affected by the magnitude of the glucose level, shown here in FIGS. 7D and 7E. Each of the slope and intercept is calculated from the regression analysis of the transients at each time point over the interferent concentrations (in the form of uric acid)/where interferent (e.g., uric acid) is the variable. FIGS. 7D and 7E show that the slopes and intercepts of these regression analyses are different for each glucose bucket (and each time point). As will be explained later, this is the reason for applicant's technique which involves first selecting a glucose range or category, and then adjusting each time point independently.

Referring back to FIG. 7D, it is noted that the slope varies for each of the time points (e.g., for the purpose of illustration, 1.05 secs, 1.10 secs, and 1.15 secs) depending on the glucose levels, such as, for example, at 50 mg/dL, 150 mg/dL, and 500 mg/dL. Similarly, with respect to FIG. 7E, the intercepts for each current transient at a particular time point (e.g., 1.05 secs, 1.10 secs, and 1.15 secs) also varied in these regions of the current transient.

Figure 8A:
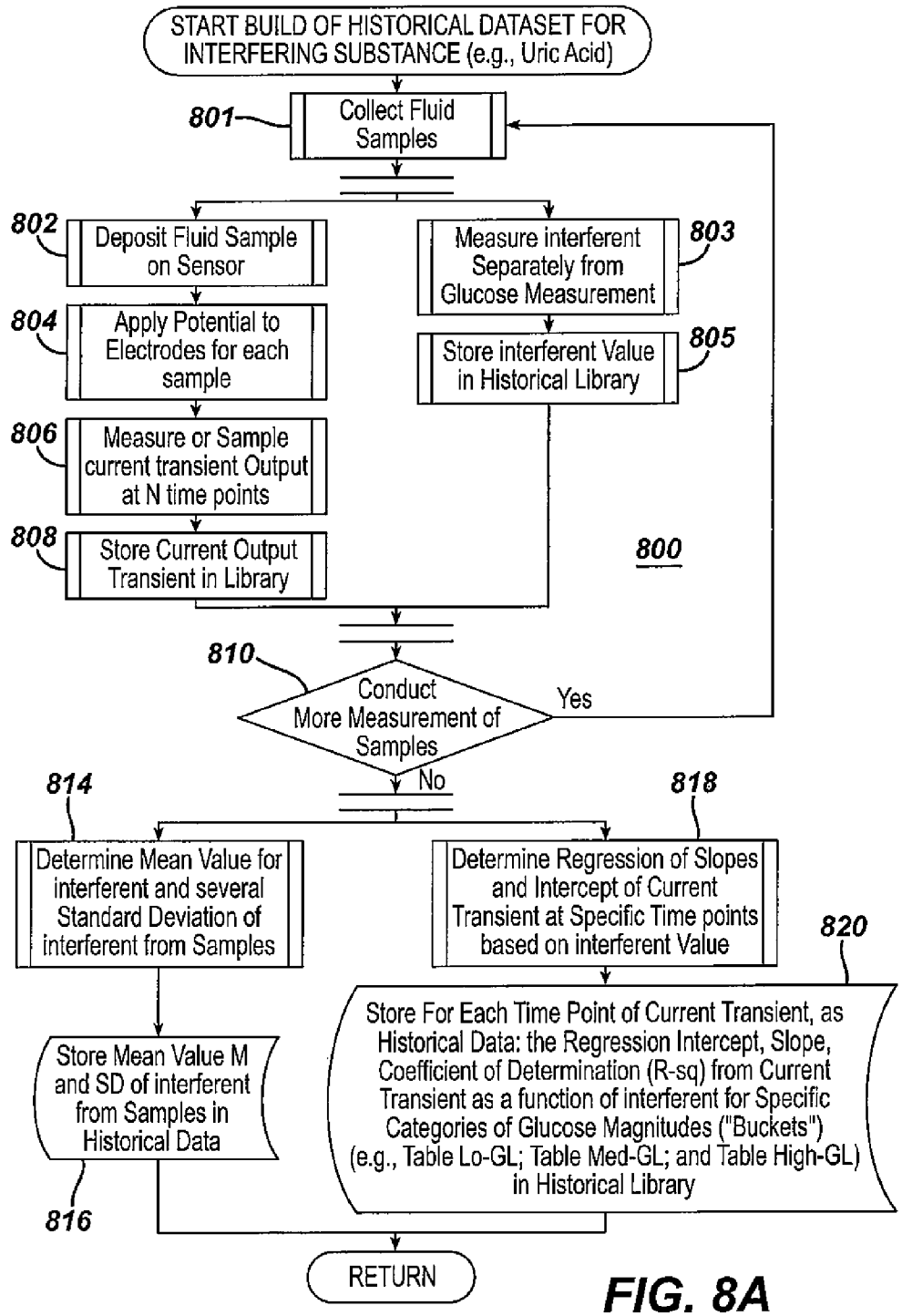
FIG. 8A illustrates an exemplary technique to generate historical data based on slopes, intercepts, and coefficients of determination of regression of current transient at specific time points during a test sequence based on interferent concentrations (in the form of uric-acid) that will be used to correct for the presence of interferent (in the form of uric-acid) that may affect the determination of glucose in the instant fluid samples of interest by the user during actual use of the glucose monitor and biosensor.

Based on these insights, applicant has arrived at a technique (and its variants) in which to estimate concentration of at least one interferent in a sample and by using that estimated value of the interferent in the sample to correct the current output transient at any time point in which a correlation with the interferent is higher than a preset correlation (or formally, a preset coefficient of determination, established through the correlation of historical data) is greater than a preset parameter such as, for example, an r-squared threshold. Specifically, this technique involves two methods. The first method builds historical data relating to certain characteristics of the biosensor with at least one interferent (or any interferent that has a good correlation with the biosensor). The second method provides an estimate of the interferent(s) (e.g., uric acid) being considered. Alternatively, the second method can be to utilize the outcome of the first method to correct for the effects of the interferent(s) (for example, uric acid) on the glucose measurement at the current transient level. Applicant will describe the first method first in relation to FIG. 8A and as referenced by logic diagram 800.

As with any historical data set building, the more test data are collected, the greater the confidence in the estimating of interferent values. As such, the first method will require that a plurality (in the hundreds or even thousands) of fluid samples be used with respective amount of biosensors by collection of the fluid samples in step 801 of FIG. 8A. For each biosensor and fluid sample, the historical data relating to current transient for glucose in physiological fluid samples can be ascertained in steps 802, 804, 806, and 808. Historical data relating to the at least one interferent in physiological fluid samples can be ascertained with steps 803 and 805 in FIG. 8A.

Referring to the collection of historical current transients (in steps 802-808), this collection begins by depositing a physiological fluid sample in a test chamber of the biosensor to start a test sequence over time interval $t_G$. The method requires the applying of a potential at step 804 to electrodes disposed in the test chamber of the biosensor over a time interval $t_G$ of the test sequence, shown specifically in FIG. 6A and at about the same time, measuring (at step 806) a current output transient CT over a plurality of time points during the time interval of the test sequence to provide a measured current output transient for each of the plurality of N time points every (approximately) 10-50 milliseconds over the time interval $t_G$, shown here in FIG. 6B. At step 808, the current transient during the test sequence is stored. The collection of interferent values begins with step 803 in which a referential interferent monitor is utilized to determine the interferent concentration (e.g., uric acid) of each sample. The referential interferent monitoring device can be ILab Aries, for instance. After the interferent concentration (e.g., uric acid) has been determined from the referential interferent monitoring device, the interferent value or concentration (e.g., uric acid) is stored in the library, and at step 810, a determination is made as to whether to obtain more data.

Assuming that there have been enough biosensors and fluid samples tested, the building of this historical library relating to the interferent begins with step 814 which is to determine a historical mean value for the interferent including values for various standards of deviations from a plurality of physiological fluid samples measured by a suitable interferent monitoring device independent from the glucose monitor. As an illustrative example, the library is provided with three categories of glucose magnitudes, from low (e.g., any glucose value less than 80 mg/dL), medium (e.g., glucose values from about 80 mg/dL to about 250 mg/dL) and high (e.g., any glucose value greater than 250 mg/dL). At step 816, the logic stores the historical mean value of the interferent in the plurality of physiological fluid samples in the historical library. At step 818, regression analysis of the current transient CT for each sample can be provided in order to obtain the slopes and intercepts at each time point during a test sequence based on the at least one interferent value.

Specifically, at each time point, the system obtains historical regression of slopes and intercepts, along with coefficient of determination of current output transient CT with respect to a test interval $t_G$ for each sample of the plurality of samples. At step 820, the system stores, for each time point of the current output transient, as historical data of the following: the regression intercept, slope, coefficient of determination (e.g., r-squared) as a function of interferent for specific categories of glucose magnitudes or "buckets" (for example the Table for Low-Glucose; Table for Medium Glucose; and Table for High Glucose) in the Historical Library. This historical data are then utilized with the logic in FIG. 8B.

Figure 8B:
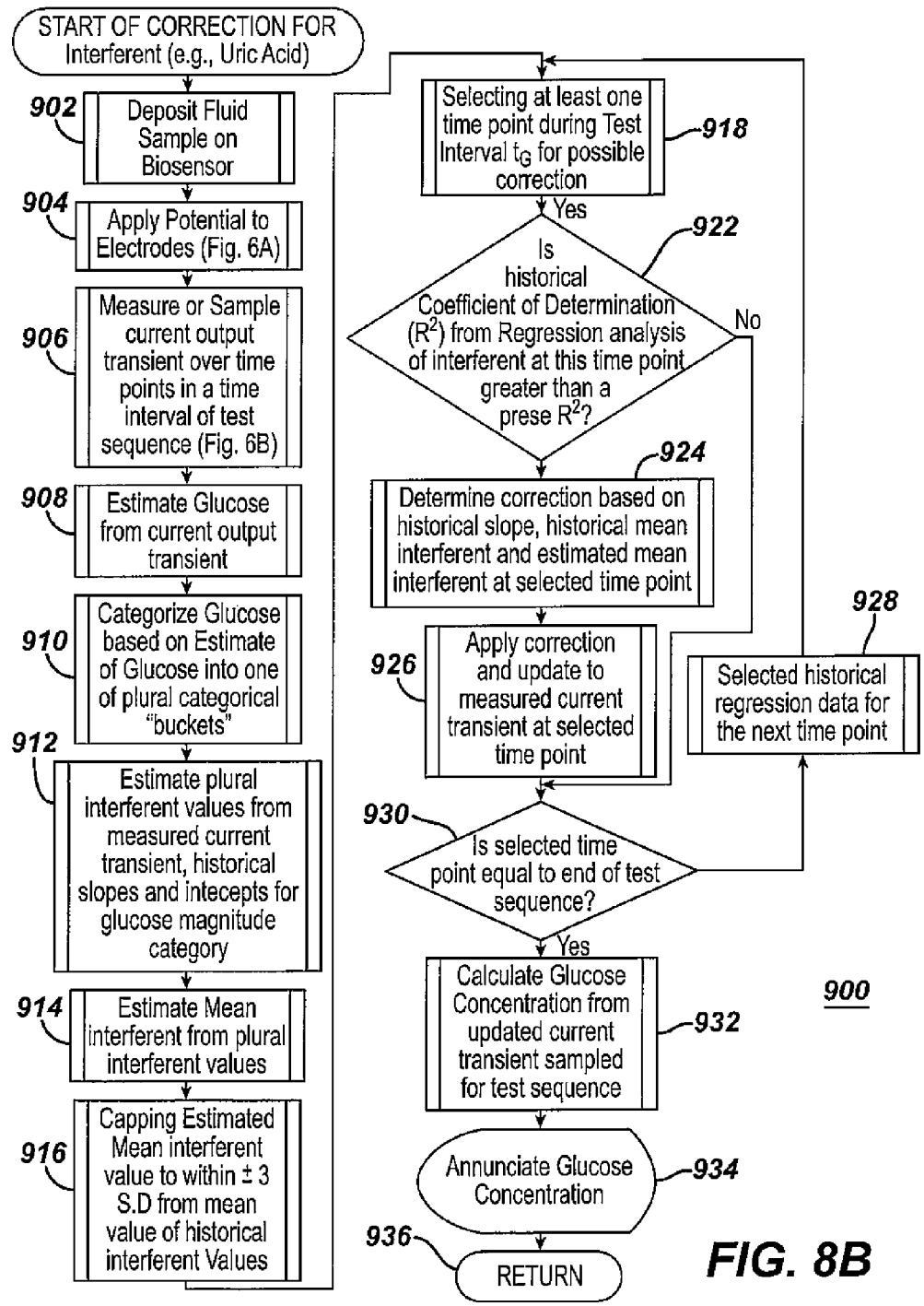
FIG. 8B illustrates an exemplary technique to correct the current output transient based on an estimation of the presence and concentration of at least one interferent (in the form of uric-acid) in a sample.

Logic 900 of FIG. 8B begins with an actual glucose measurement, namely by depositing a physiological fluid sample in a test chamber of the biosensor to start a test sequence. Before deposition of the sample (or even after deposition of the sample) in step 902, the system can apply, at step 904 a plurality of potentials (e.g., E1, E2, E3 in FIG. 6A) to electrodes disposed in the test chamber of the biosensor over a time interval $t_G$ of the test sequence (FIG. 6A). At step 906, the system measures a current output transient CT over a plurality of time points during the time interval $t_G$ of the test sequence to provide a measured current output transient CT for each of the plurality of time points during interval $t_G$ (FIG. 6B). From Equations 5, 5.1, and 5.2, the system estimates, at step 908, an uncorrected (or estimated) glucose value of the fluid sample from the measured current output transient CT of the measuring step. It is noted that step 908 allows the system to categorize the estimated glucose into a "bucket" or one of plural distinct categories of glucose magnitudes, such as, for example, "low glucose" (e.g., less than 80 mg/dL for illustrative purposes), "medium glucose" (e.g., greater than 80 mg/dL and less than 250 mg/dL for illustrative purposes) and "high glucose" (e.g., greater than 250 mg/dL for illustrative purposes). Once the estimated glucose has been categorized in step 908, the system can now estimate the interferent's concentration from the historical library that has been built (in FIG. 8A) for glucose values similar to the estimated glucose.

For illustrative purposes, it is assumed that the estimated glucose is about 50 mg/dL. This means that historical data for a historical glucose value of 50 mg/dL can be used to correct for the interferent that is present in the instant glucose result. One example of such historical data is shown in Table 1 of the Appendix.

In Table 1 of the Appendix, historical data regarding slopes, intercepts, and coefficients of determination for a low glucose result are tabulated with respect to each time point at an interval of about 50 milliseconds over the time interval $t_G$. As a result, over the test sequence time of about 5 seconds, approximately 100 current output values are sampled from the transient CT of FIG. 6B for each of the slopes, intercepts, and coefficients of determination. Because of the large amount of data, and because the strength of the correlation between transient and interferent concentration varies across the test sequence time, it has been determined that certain thresholds should be utilized to reduce the large amount of data to a manageable load. Based on applicant's analysis, the threshold can be from about 50% to about 80%. In this example for a glucose estimate of approximately 50 mg/dL, the threshold has been set to about 50%, which means that eighteen time points (all time points between 1.05 sec and 1.90 sec included) need to be corrected before being used again in Equations 5, 5.1 and 5.2 to provide for the interferent-corrected glucose result.

Referring back to step 914, the estimating of a plurality of interferent values at specific time points is based on: (a) the measured current output transient; and (b) historical slopes and historical intercepts of current transient output for historical interferent values that have been collected in the one category of glucose magnitudes (e.g., low glucose of Table 1). Specifically, the estimation is based on the regression and slope of the dataset built beforehand (e.g., FIG. 8A and Table 1) and on the glucose bucket (referred to as $GL_{Group}$) defined in the previous subsection so that the estimated interferent concentration can be defined by Equation 6:

$$EstimatedInterferent(GL_{Group}, t) = \frac{Current(GL_{Group}, t) - Intercept(GL_{Group}, t)}{Slope(GL_{Group}, t)} \quad \text{Eq. 6}$$

where
- EstimatedInterferent($GL_{Group}$, t) is the estimated interferent concentration in mmol/L or mmol*$L^{-1}$;
- Current($GL_{Group}$, t) is a current magnitude (in microamps) measured at time point t of the instant sample being evaluated;
- Intercept($GL_{Group}$,t) is the magnitude in microamps of the historical intercept measured at time point t from regression analysis of historical data of the appropriate glucose category;
- Slope($GL_{Group}$, t) is the magnitude in microamps per millimol/liter or microamp*$mmol^{-1}$ *L of the historical slope measured at time point t from regression analysis of historical data of the appropriate glucose category.

As an example, a transient CT has been utilized to estimate the glucose result as being amongst the "Low" glucose "bucket". Since the glucose estimate indicates that the sample belongs to the "Low" glucose "bucket", three estimations of uric acid concentration are computed from measured current transient at 1.05 secs (~11.71 microamps), 1.1 secs (~5.17 microamps), 1.15 secs (~3.49 microamps) and historical data of Table 1 (Appendix) having Slopes (at 1.05, 1.1 and 1.15 secs) and Intercepts (at 1.05, 1.1, and 1.15 secs) at each of the relevant time points (e.g., 3 time points in this example) in which the coefficient of determination is the most relevant.

$$EstimatedUricAcid(LowGL, t = 1.05 \text{ sec}) =$$
$$\frac{11.71 - 8.69}{18.57} = 0.163 \text{ mmol} \cdot L^{-1}$$

$$EstimatedUricAcid(LowGL, t = 1.10 \text{ sec}) =$$
$$\frac{5.17 - 4.04}{11.79} = 0.096 \text{ mmol} \cdot L^{-1}$$

$$EstimatedUricAcid(LowGL, t = 1.15 \text{ sec}) =$$
$$\frac{3.49 - 42.79}{9.34} = 0.074 \text{ mmol} \cdot L^{-1}$$

While the estimated interferent concentration at anyone of these three time points can be used, it is preferable that an average be used to offset any outlier result for step 918. This average will now be set as the "estimated interferent" concentration and will be used interchangeably with "estimated mean interferent" concentration for the particular interferent in this case of "uric acid."

$$EstimatedUricAcid = \frac{0.163 + 0.096 + 0.074}{3} = 0.111 \text{ mmol} \cdot L^{-1}$$

The correcting of the measured current output transient is based on: (a) the measured current output transient at the specific time points during the test sequence, (b) the historical slope at the specific time points during the test sequence from historical data, and (c) historical mean interferent value and (d) estimated mean interferent value of the estimating step. As an example with the exemplary biosensor system and uric acid as the subject interferent for the low glucose category, the correcting of the current transient at these exemplary eighteen time points (from 1.05-1.9 secs of Table 1 of Appendix where R-squared>50%) can be via steps 920, 922, 924, 926, 928 and 930. To recap, time points are selected for interferent-concentration (e.g., uric-acid) estimation whenever the correlation is the most relevant in the historical current transient (e.g., FIGS. 7A-7C). Once the interferent concentration has been estimated, all of the time points for the current transient in the historical library is considered with respect to a predetermined threshold (e.g., 50%-80% or R-squared) and time points at or above the threshold (e.g., R-squared) will be selected as the bases for correction to the actual current transient of the subject sample. In the example described here for the low-glucose bucket, the current transient of FIG. 7A is considered and three time points (≈1.05-1.15 secs) show the highest correlation with the subject interferent uric-acid and these three time points will be used to provide an estimated interferent. To correct the current transient of the actual measurement with the estimated interferent, the system looks at time points that are at or above the predetermined threshold (R-squared of ≈50%) for the low-glucose category. As can be seen in the historical library (e.g., Table 1 of the Appendix), there are numerous time points from about 1.05 secs to about 1.9 secs that have the coefficient of determination above 50%. As the current transient is sampled every fifty milliseconds in the exemplary embodiments, there are eighteen time points that will be used for correction (due to the estimated interferent concentration) to the actual current transient at the corresponding actual time points.

Once the corrected current transient at these specific time points have been determined, the system calculates a glucose concentration corrected for the presence of the interferent based on the measured current output transient that includes the corrected current output transient at the specific time points from the correcting step.

It is noted that the correcting steps may include step 920 which is to cap the estimated interferent value so that the estimated mean interferent value is within ±3 standard deviations of historical mean value of interferent concentrations. This capping or limiting or limiting is done in order to avoid erroneous estimations, which might occur if extreme values for current at these time points were recorded. Assuming a normal distribution of interferent levels, 99.7% of values are within three standard deviations away from the mean. In reality, the distribution of interferent is slightly skewed in the population, but a very large portion of the population would still be contained in that range of MeanInterferent±3 SDs.

Consequently, all computed values of estimated interferent concentration falling outside are replaced with the corresponding "limit" defined by the following if-then statement in logic 900:

IF EstimatedInterferent<MeanInterferent then set EstimatedInterferent=maximum(EstimatedInterferent, MeanInterferent−3*SD) else set
EstimatedInterferent=minimum(EstimatedInterferent, MeanInterferent+3*SD)

Therefore, as applied to the example described here for uric acid, there would be no change to the estimated interferent (from step 918) as the following calculation shows that the "estimated mean interferent" (in this example, "mean uric-acid") is within the range:
MeanUricAcid=0.334 mmo/$l^{-1}$; SD=0.9 lmmol·$L^{-1}$
MeanUricAcid−3*SD=0.063<EstimatedUricAcid=0.111 mmol·$L^{-1}$
and EstimatedUricAcid=0.111 mmol·L$^{-1}$<MeanUricAcid+ 3*SD=0.61 mmol·L$^{-1}$
⇒ NO-CHANGE Once this capping or limiting or limiting step has been performed, the resulting estimated mean interferent concentration is set aside so that the logic could determine if there is a need for correction. Specifically, at step 922, the logic evaluates as to whether a historical coefficient of determination (from regression analysis of historical interferent values) at each of the plurality of time points during interval $t_G$ that have been collected in a test sequence—for the one category of glucose magnitudes—is greater than a predetermined threshold, such as, for example, an R-squared value. If the evaluating step returns a "yes", the logic applies a correction to the current output transient for each of the plurality of time points that has a historical coefficient of determination greater than the predetermined R-squared value.

Alternatively, if the evaluating step returns a "no", then the system performs a selecting of another time point and returning to the evaluating step until all of the coefficients of determinations for all of the time points in the test sequence have been considered against the predetermined r-squared threshold.

In other words, for a given glucose concentration, all time points corresponding to R-Sq values above this threshold in the regression triplets (slope, intercept, R-Sq value) in the "library" (e.g., Table 1, 2, or 3) will be corrected. It must be noted that every time point in the transient is considered individually. As a result, the corrective process is applied to the current at such specific time points only (for a given glucose concentration) so that the correction computed to the current transient at such time point is unique to each time point. For each time point, the R-Sq value in the regression "historical library" is compared to the R-Sq threshold: If the R-Sq value for this time point is less than the parameter/threshold value, then the current at this time point will be left as such and will not be corrected for interferent.

On the contrary, if the R-Sq value for this time point is greater than the parameter/threshold value, then a correction will be computed and applied to the current value at this time point in the transient. The correction is computed in order to "normalise" the current value towards a more "interferent-neutral" value, corresponding to what it would have been, had the interferent concentration in the blood sample been equal to the mean interferent level in the population (the population refers here to the pool of donors used to build the regression "library").

In this example, the historical regression current which is a function of the historical slope, intercepts and historical mean interferent value, for each time point of the test sequence, is defined in Equation 7 as:

$$\text{Current}_{Regression}(GL,t)=\text{Slope}(GL_{Group},t)*\text{MeanInterferent}+\text{Intercept}(GL_{Group},t) \qquad \text{Eq. 7}$$

The measured current at each time point of the test sequence is defined as a function of the historical slope, intercept, estimated interferent and regression error, shown here in Equation 8.

$$\text{Current}_{Measured}(GL,t)=\text{Slope}(GL_{Group},t)*\text{Estimated-Interferent}+\text{Intercept}(GL_{Group},t)+\text{Error}(t) \qquad \text{Eq. 8}$$

From these two equations, the corrected current output transient, at each time point, is based on regression parameters (or historical data of Table 1, 2, or 3 for historical slopes and intercepts in the Appendix), the historical mean interferent value and regression error, shown here in Equation 9.

$$\text{Current}_{Corrected}(GL,t)=\text{Slope}_{Group},t)*\text{MeanInterferent}+\text{Intercept}(GL_{Group},t)+\text{Error}(t) \qquad \text{Eq. 9}$$

Hence, by adjusting this relationship (i.e., by "centering") based on the estimated interferent concentration (from step 918), applicant is able to shift the actual current transient output at a specific time point "t" so as to reduce the effect of the interferent on the actual current output transient. By reducing or eliminating the effect of interferent on the current output transient, the current transient is now accurately reflective of the concentration of glucose in the measured sample. Equation 10 allows for the correction of the current transient output at one or more specific time points "t" during interval $t_G$.

$$\text{Current}_{Corrected}(GL,t)=\text{Current}_{Measured}(GL_{Group},t)+\text{Slope}(GL_{Group},t)*(\text{MeanInterferent}-\text{EstimatedInterferent}) \qquad \text{Eq. 10}$$

Assuming that the measured current output transient at about 1.05 seconds for the instant sample is about 11.71 microamps, the system will look up the historical library for the historical slope (18.574 microamp/(mmol/L) from Table 1) and historical mean uric acid value (~0.334 mmol/L) and the estimated mean uric acid (0.111 mmol/L from step 918). Applying Equation 10 to these values, the corrected current output transient at about 1.05 seconds or "Current$_{Corrected}$ (atLowGL, t)" for the instant fluid sample is:

Current$_{Corrected}$(atLowGL,t=1.05sec.)=11.71+18.57*(0.334−0.111)=15.86 microamps It is noted that all values of the original transient for the time points "t" from 0 to 5 seconds (with an interval of 50 milliseconds) may not have been corrected. Nevertheless, the new set of current values (with corrected and uncorrected values) will be referred to as the "corrected transient".

At step 932, these current output transients during the test sequence, including the corrected current transients at specific time points will then be used in Equations 5, 5.1 and 5.2 to arrive at a glucose result that is virtually unaffected by the interfering effects of the interferent on the biosensor chemistries. At step 934, the result will then be annunciated to the user or stored for future analysis.

Applicant notes that the efficiency of this correction technique has been tested on several datasets completely independent from the initial dataset on which the regression slope and intercept "libraries" have been built, in order to assess the robustness of the technique (and its variants). Five sets of data, for which current output transients for the commercial version of the biosensor system described herein had been collected, have been analysed with regards to the interferent correction technique presented here. The first two studies concentrate on identified levels of interferent such as, for example, uric-acid, in physiological samples such as blood. The third set of data has been built with controlled samples (in terms of glucose concentration, with specified range of Haematocrit and Oxygen levels), while the last two sets of data contain "natural" patient samples.

As used herein, "B/% B" stands for Bias/Bias %, where "Bias" indicates the bias of meter reading to YSI reference for glucose concentrations less than 80 mg/dL, and where "Bias %" indicates percent bias of meter reading to YSI reference for glucose concentrations greater than 80 mg/dL. "Corr 0.50" indicates that a correction has been applied using the algorithm described above, with an "R-Sq Threshold" parameter value of 0.50 selected.

First Study

A study has been conducted with blood samples from five donors which have been spiked to six different glucose levels, and adjusted for five different haematocrit levels. Two of the donors had naturally low levels of a particular interferent of interest in the form of uric-acid while the other three donors had "normal" to "high" levels of uric acid. Tests have been conducted with three batches. The original glucose results showed poor results for low glucose/high Hematocrits ("Hct") for the two donors which showed naturally low levels of uric acid (Donor #2 and Donor #4). When the correction technique is applied, the erroneous readings are successfully corrected and pass the accuracy criteria, shown here in Table A.

As can be seen in Table A, applicant's technique was able to achieve 98.8% accuracy to referential datum (YSI) for a sample that was less than 89%. The technique was even better for one result that was less than 80% accurate by achieving 100% accuracy relative to referential datum (YSI).

TABLE A

Accuracy statistics per Glucose Level and per Haematocrit Level across three batches, comparing the bias/% bias to YSI values of original meter reading and algorithm-corrected readings (In-House Study).

| glucose concentration (mg/dL) | Haematocrit (%) | N | Accuracy (12 mg/dL/ 80 mg/dL/15%) | |
|---|---|---|---|---|
| | | | Original | Corrected |
| 40 | 19 | 174 | 100.00% | 100.00% |
| 40 | 30 | 186 | 100.00% | 98.92% |
| 40 | 42 | 180 | 100.00% | 100.00% |
| 40 | 50 | 173 | 100.00% | 100.00% |
| 40 | 61 | 178 | 88.20% | 98.88% |
| 65 | 19 | 180 | 100.00% | 100.00% |
| 65 | 30 | 156 | 100.00% | 100.00% |
| 65 | 42 | 173 | 100.00% | 100.00% |
| 65 | 50 | 180 | 98.89% | 100.00% |
| 65 | 61 | 179 | 78.77% | 100.00% |
| 120 | 19 | 180 | 100.00% | 99.44% |
| 120 | 30 | 173 | 100.00% | 100.00% |
| 120 | 42 | 181 | 100.00% | 100.00% |
| 120 | 50 | 168 | 98.81% | 100.00% |
| 120 | 61 | 167 | 97.60% | 100.00% |

TABLE A-continued

Accuracy statistics per Glucose Level and per Haematocrit Level across three batches, comparing the bias/% bias to YSI values of original meter reading and algorithm-corrected readings (In-House Study).

| glucose concentration (mg/dL) | Haematocrit (%) | N | Accuracy (12 mg/dL/ 80 mg/dL/15%) | |
|---|---|---|---|---|
| | | | Original | Corrected |
| 350 | 19 | 179 | 100.00% | 100.00% |
| 350 | 30 | 174 | 100.00% | 100.00% |
| 350 | 42 | 180 | 100.00% | 100.00% |
| 350 | 50 | 192 | 100.00% | 100.00% |
| 350 | 61 | 180 | 100.00% | 100.00% |
| 560 | 19 | 185 | 100.00% | 100.00% |
| 560 | 30 | 174 | 100.00% | 100.00% |
| 560 | 42 | 173 | 100.00% | 100.00% |
| 560 | 50 | 177 | 100.00% | 100.00% |
| 560 | 61 | 144 | 100.00% | 99.31% |

Second Study

A study was conducted using blood of one donor with naturally occurring low level of a particular interferent of interest in the form of uric-acid. With haematocrit adjusted to 61%, tests were conducted on commercial version of the exemplary biosensors in five batches across two glucose levels (60 mg/dL and 560 mg/dL) and two levels of uric acid (the "natural" low level, and a high level of uric acid where the sample has been spiked by adding 5.88 mg/dL of uric acid).

While the original glucose results showed very poor results at low glucose for "natural" blood (with low uric acid level), the application of the correction technique presented earlier significantly improves the results. It corrects for the erroneous elevated bias at low glucose and passes the accuracy requirements, which can be seen here in the highlighted results in Table B and Table C.

TABLE B

Means, SDs and Accuracy statistics per glucose concentration, per Blood Type (with regards to uric acid levels) and per batch, comparing the bias/% bias to YSI values of original meter reading and uric-corrected readings (In-House Study)

| glucose concentration (mg/dL) | Blood Type (uric acid) | Batch | N | Mean B/% B | | Standard Deviation | | Accuracy (12 mg/dL/80 mg/dL/15%) | |
|---|---|---|---|---|---|---|---|---|---|
| | | | | Original | Corrected | Original | Corrected | Original | Corrected |
| 60 | Natural | 3079500 | 12 | 15.545 | 5.878 | 3.720 | 5.143 | 0.00% | 91.67% |
| 60 | Natural | 3088300 | 12 | 12.045 | 1.212 | 1.865 | 1.564 | 58.33% | 100.00% |
| 60 | Natural | 3096300 | 12 | 12.212 | 1.878 | 1.621 | 1.379 | 66.67% | 100.00% |
| 60 | Natural | 3291600 | 12 | 5.545 | −4.538 | 0.965 | 0.985 | 100.00% | 100.00% |
| 60 | UA Spiked | 3079500 | 6 | 4.128 | 3.128 | 1.033 | 1.033 | 100.00% | 100.00% |
| 60 | UA Spiked | 3088300 | 12 | 4.545 | 3.545 | 1.545 | 1.815 | 100.00% | 100.00% |
| 60 | UA Spiked | 3096300 | 12 | 3.712 | 2.295 | 1.311 | 1.624 | 100.00% | 100.00% |
| 60 | UA Spiked | 3291600 | 12 | −2.955 | −3.122 | 2.340 | 2.575 | 100.00% | 100.00% |
| 560 | Natural | 3079500 | 12 | −0.552 | −1.594 | 3.564 | 3.518 | 100.00% | 100.00% |
| 560 | Natural | 3088300 | 12 | 3.494 | 2.268 | 4.411 | 4.255 | 100.00% | 100.00% |
| 560 | Natural | 3096300 | 12 | 0.414 | −0.674 | 2.407 | 2.348 | 100.00% | 100.00% |
| 560 | Natural | 3291600 | 12 | −2.851 | −3.969 | 2.790 | 2.735 | 100.00% | 100.00% |
| 560 | UA Spiked | 3079500 | 12 | −2.667 | −2.483 | 4.006 | 3.929 | 100.00% | 100.00% |
| 560 | UA Spiked | 3088300 | 12 | 0.414 | 0.276 | 3.356 | 3.372 | 100.00% | 100.00% |
| 560 | UA Spiked | 3096300 | 12 | −3.663 | −3.862 | 3.312 | 3.262 | 100.00% | 100.00% |
| 560 | UA Spiked | 3291600 | 6 | −4.766 | −4.705 | 2.989 | 2.930 | 100.00% | 100.00% |

TABLE C

Means, SDs and Accuracy statistics per glucose concentration and per Blood Type (with regards to uric acid levels) across batches, comparing the bias/% bias to YSI values of original meter reading and uric-corrected readings (In-House Study)

| glucose concentration (mg/dL) | Blood Type (uric acid) | N | Mean B/% B | | Standard Deviation | | Accuracy (12 mg/dL/80 mg/dL/15%) | |
|---|---|---|---|---|---|---|---|---|
| | | | Original | Corrected | Original | Corrected | Original | Corrected |
| 60 | Natural | 48 | 11.337 | 1.108 | 4.277 | 4.641 | 56.250% | 97.917% |
| 60 | UA Spike | 42 | 2.105 | 1.224 | 3.646 | 3.387 | 100.000% | 100.000% |
| 560 | Natural | 48 | 0.126 | −0.992 | 4.000 | 3.908 | 100.000% | 100.000% |
| 560 | UA Spiked | 42 | −2.371 | −2.406 | 3.871 | 3.820 | 100.000% | 100.000% |

Third Study

A third study was conducted over 10 days and involved, in particular: 12 donors per day, 6 glucose levels, with Hematocrits or Hct between 38% and 46%), with 78 batches, and corresponding transients collected from the study for use as dataset.

Samples in this dataset where partly controlled. Donors for this study are non-diabetic. Only donors with Hematocrits between 38% and 46% were selected. Oxygen levels are also measured on each blood sample before and after testing. The oxygen levels are controlled so that they remain between 7.0 and 9.0 kPa.

From Table D, it is apparent that there is no significant difference between the bias to YSI reference of the original meter readings and of algorithm-corrected readings for this set of data, which can indicate that on "standard" populations, the exemplary technique may have no or little effect.

TABLE D

Means, SDs, Variances and Accuracy statistics comparing the bias/% bias to YSI reference of original meter reading and algorithm-corrected readings

| glucose concentration (mg/dlL) | N | Quick Stats | | | | | | Accuracy (12/15/80) | |
|---|---|---|---|---|---|---|---|---|---|
| | | Mean | | Standard Dev | | Variance | | % in Spec | |
| | | Original | Corrected | Original | Corrected | Original | Corrected | Original | Corrected |
| 50 | 3463 | 0.377 | 0.009 | 3.116 | 3.070 | 9.711 | 9.423 | 99.94% | 99.91% |
| 100 | 3126 | −0.292 | −0.236 | 3.756 | 3.385 | 14.107 | 11.459 | 99.97% | 99.97% |
| 150 | 3103 | −1.027 | −1.205 | 3.502 | 3.371 | 12.262 | 11.366 | 99.87% | 99.84% |
| 200 | 3146 | −1.111 | −1.417 | 3.754 | 3.514 | 14.089 | 12.345 | 99.97% | 99.94% |
| 300 | 3406 | −0.422 | −0.428 | 3.917 | 3.734 | 15.344 | 13.946 | 99.94% | 99.97% |
| 500 | 3412 | −1.507 | −1.591 | 4.207 | 4.167 | 17.701 | 17.364 | 99.85% | 99.88% |

Fourth Study

Results from five different clinic studies were pooled together to form a large dataset of meter readings for diabetic patients across a relatively large number of batches (forty-two batches).

TABLE E

Means, SDs, Variances and Accuracy statistics comparing the bias/% bias to YSI reference of original meter reading and algorithm-corrected readings

| glucose concentration (mg/dL) | N | Quick Stats | | | | | | Accuracy (12/15/80) % in Spec | |
|---|---|---|---|---|---|---|---|---|---|
| | | Mean | | Standard Dev | | Variance | | | |
| | | Original | Corrected | Original | Corrected | Original | Corrected | Original | Corrected |
| <80 | 216 | 3.623 | 4.720 | 6.622 | 5.380 | 43.855 | 28.948 | 90.74% | 95.37% |
| ≥80 | 4002 | 0.876 | 1.118 | 6.903 | 6.248 | 47.645 | 39.032 | 97.15% | 97.90% |

TABLE F

Comparison of Pooled within donor Standard
Deviation and Standard Deviation across Mean
per Donor between the bias/% bias to YSI reference
of original meter reading and algorithm-corrected
readings

|  | Original | Corrected |
|---|---|---|
| Pooled Within Donor SD | 5.531 | 5.113 |
| Donor to Donor Variation (SD across Mean Donor) | 6.359 | 5.917 |

Figure 9A:
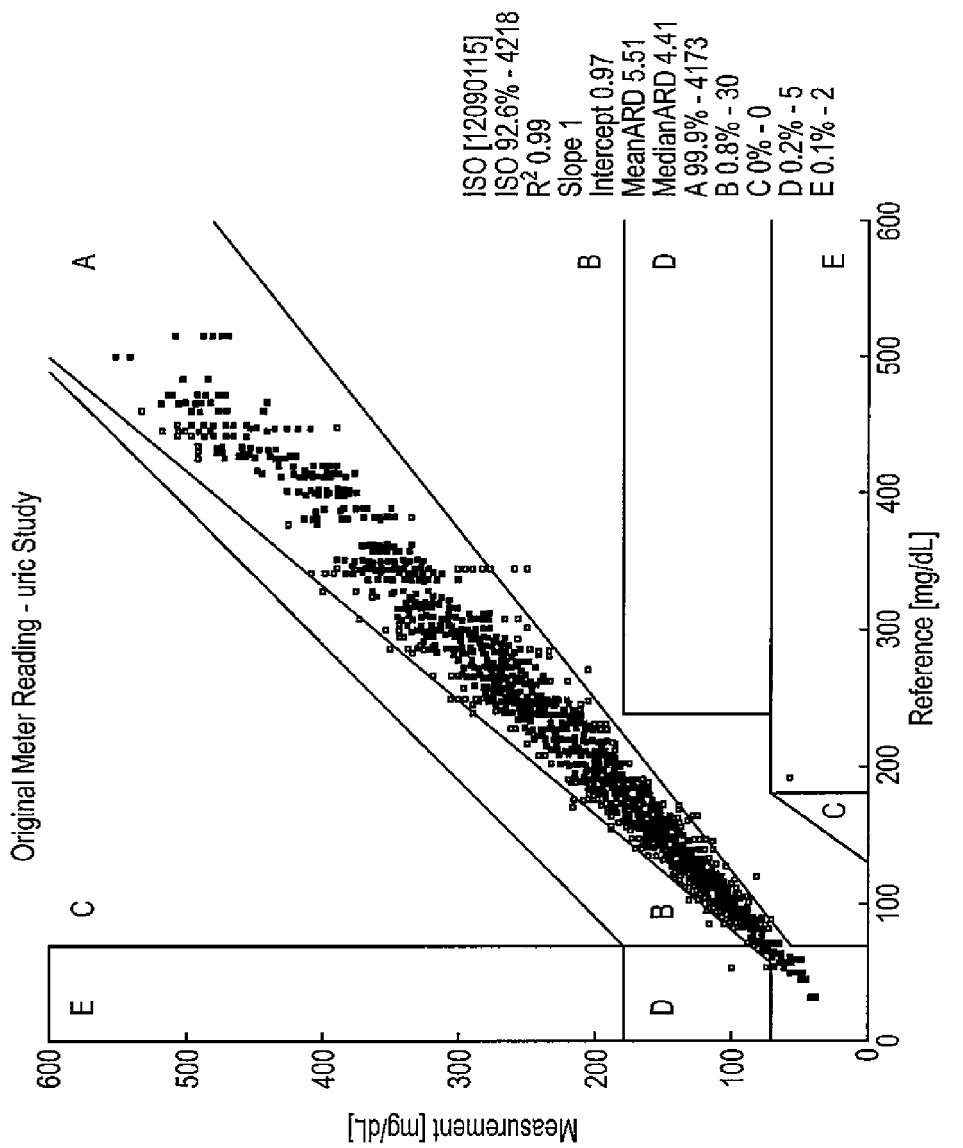
FIG. 9A is a Clarke-Grid for uncorrected glucose measurements in the fourth study with YSI referential datum.
Figure 9B:
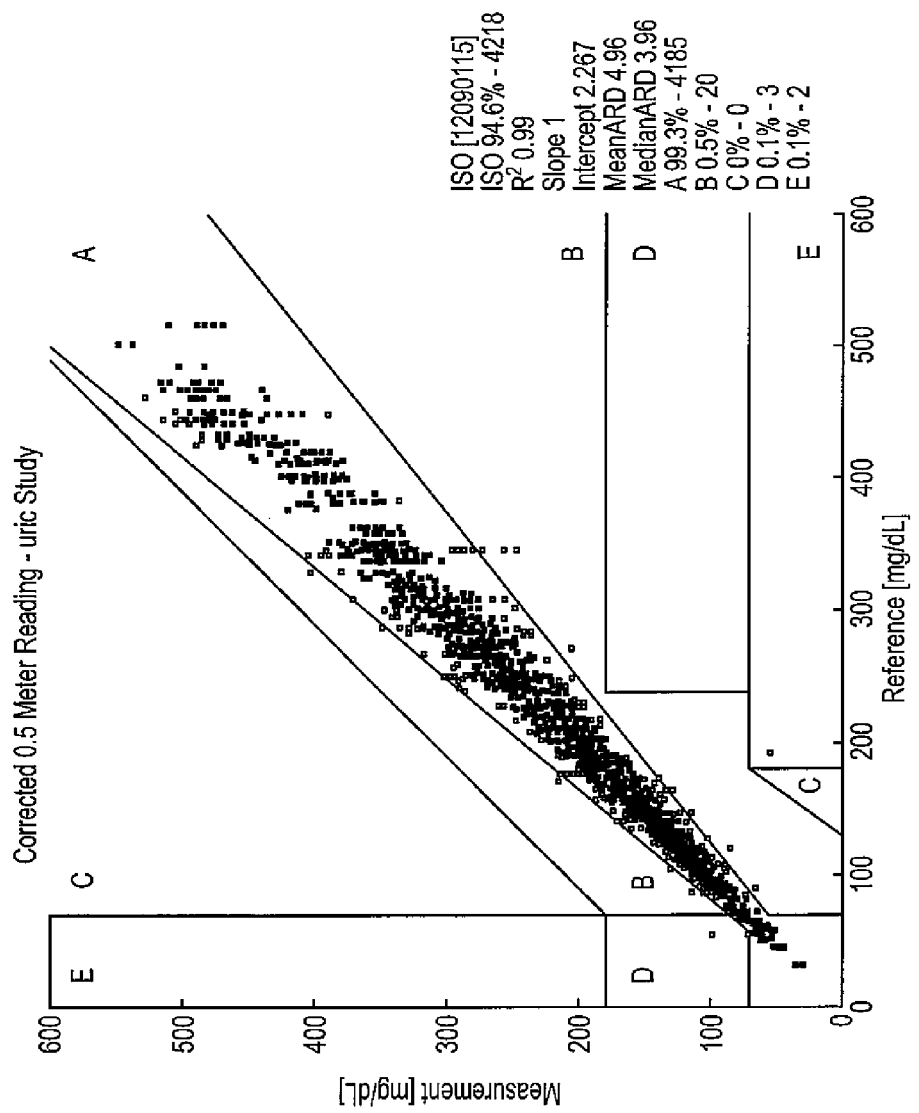
FIG. 9B is a Clarke-Grid for corrected glucose measurements of the fourth study with YSI referential datum.

The correction technique improves the accuracy of commercial version of the exemplary biosensor at low glucose in particular. It significantly reduces donor-to-donor variation, contributing to a better precision. The lesser dispersion of data points can be observed on the "Clarke plots" of FIGS. 9A and 9B.

Fifth Study

Data were collected in 2009 on newborns that are believed to have natural low levels of uric acid, as well as low level of glycaemia. While the original readings showed relatively poor results at low glucose (<80 mg/dL) with elevated bias to YSI reference, the application of the applicant's correction technique presented earlier improves significantly the results in terms of mean bias and, consequently, accuracy.

TABLE G

Means, SDs and Accuracy statistics comparing the bias/% bias to YSI
reference of original meter reading and algorithm-corrected readings

| glucose concentration (mg/dL) | N | Mean | | Standard Dev | | Accuracy (12/15/80) % in Spec | |
|---|---|---|---|---|---|---|---|
| | | Original | Corrected | Original | Corrected | Original | Corrected |
| <80 | 148 | 9.055 | 5.630 | 4.206 | 3.796 | 72.97% | 94.59% |
| ≥80 | 15 | 11.830 | 8.756 | 11.510 | 10.284 | 66.67% | 73.33% |

FIG. 10 illustrates the results from Table G. While the bias to YSI reference of original glucose measurements was extremely high for lower glucose values (<80 mg/dL), the bias to YSI reference of corrected glucose measurements have been brought back to more acceptable values. In particular, it can be noticed in FIG. 10 that the mean bias to YSI has shifted from approximately 9 mg/dL to about 5.6 mg/dL.

For higher glucose values (>80 mg/dL), the mean bias % is also lowered from over 11 mg/dL to about 10 mg/dL. Nevertheless, the very few number of sampled in this category (15) make it difficult to conclusions.

Overall, it can also be noticed that for both the bias and bias % to YSI reference, the individual values are not as spread for the corrected glucose measurement as for the original values, illustrating the gain in precision.

While the invention has been described in terms of particular variations and illustrative figures, those of ordinary skill in the art will recognize that the invention is not limited to the variations or figures described. As an example, applicant has demonstrated the technique using one type of interfering substance in the form of uric acid. Nevertheless, corrections can also be made for other types of interfering substances besides uric acid. As such, it is the intent of applicant that this technique be fully applicable to other interfering substances and that the technique cannot be so limited to just uric acid. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining an interferent corrected glucose concentration from a fluid sample with a glucose monitor and a biosensor, the method comprising the steps of:
   ascertaining historical data relating to at least one interferent in physiological fluid samples by:
   determining a historical mean concentration for the at least one interferent including various standards of deviations from a plurality of physiological fluid samples measured separately by a referential interferent sensor at various glucose concentrations;
   storing the historical mean concentration of the at least one interferent in the plurality of physiological fluid samples;
   measuring a current output transient of each of the plurality of the physiological fluid samples with respect to time points during a test sequence; and
   obtaining historical regression of slopes and intercepts, along with coefficients of determination of the current output transient at corresponding time points with respect to the test interval for each sample of the plurality of samples; and
   retaining as historical data for each time point of the current transient of each of the physiological samples, the following parameters from regression analyses as a function of the at least one interferent concentration at each specific glucose concentration: (a) regression slope, (b) regression intercept, and (c) coefficient of determination associated with the regression slope and regression intercept;
   depositing a physiological fluid sample in a test chamber of the biosensor to start a test sequence;
   applying a plurality of potentials to electrodes disposed in the test chamber of the biosensor over a time interval of the test sequence;
   measuring a current output transient over a plurality of time points during the time interval of the test sequence to provide a measured current output transient for each of the plurality of time points;
   estimating a glucose concentration of a fluid sample from the measured current output transient of the measuring step;
   categorizing the estimated glucose concentration into one of plural distinct categories of glucose magnitudes;
   estimating a plurality of the at least one interferent concentrations at specific time points based on: (a) the measured current output transient; and (b) historical slopes and historical intercepts of current transient output for historical interferent concentrations that have been collected in the one category of glucose magnitudes;
   determining an estimated mean interferent concentration from the plurality of estimated interferent concentrations from the estimating step;
   correcting the measured current output transient based on: (a) the measured current output transient at the specific time points during the test sequence, (b) the historical slope at the specific time points during the test sequence from historical data, and (c) historical mean interferent concentration and (d) estimated mean interferent concentration of the estimating step; and calculating a glucose concentration corrected for the presence of at least one interferent based on the measured current output transient that includes the corrected current output transient at the specific time points from the correcting step.

2. A method of determining glucose concentration corrected for presence of interferent from a fluid sample with a glucose monitor and a biosensor, the method comprising the steps of:

depositing a physiological fluid sample in a test chamber of the biosensor to start a test sequence;

applying a plurality of potentials to electrodes disposed in the test chamber of the biosensor over a time interval of the test sequence;

measuring a current output transient over a plurality of time points during the time interval of the test sequence to provide a measured current output transient for each of the plurality of time points;

estimating a glucose concentration of a fluid sample from the measured current output transient of the measuring step;

categorizing the estimated glucose concentration into one of plural distinct categories of glucose magnitudes;

estimating a plurality of at least one interferent concentrations at specific time points based on: (a) the measured current output transient; and (b) historical slopes and historical intercepts of current transient output for historical interferent concentrations that have been collected in the one category of glucose magnitudes;

determining an estimated mean of the at least one interferent concentration from the plurality of estimated interferent concentrations from the estimating step;

correcting the measured current output transient based on: (a) the measured current output transient at the specific time points during the test sequence, (b) the historical slope at the specific time points during the test sequence from historical data, and (c) a historical mean interferent concentration from historical data and (d) estimated mean interferent concentration of the estimating step; and calculating a glucose concentration corrected for the presence of the at least one interferent based on the measured current output transient that includes the corrected current output transient at the specific time points from the correcting step.

3. The method of claim 2, further comprising:

ascertaining historical data relating to the at least one interferent in physiological fluid samples by:

determining a mean concentration for the at least one interferent from a plurality of physiological fluid samples measured separately by a referential interferent sensor at various glucose concentrations;

storing the mean concentration of at least one interferent in the plurality of physiological fluid samples; and obtaining historical regression of slopes and intercepts, along with coefficients of determination of current output transient at corresponding time points with respect to a test interval for each sample of the plurality of samples; and retaining as historical data for each time point of the current transient of each of the physiological samples, the following parameters from regression analyses as a function of the at least one interferent concentration at each specific glucose concentration: (a) a regression slope, (b) a regression intercept, and (c) a coefficient of determination associated with the regression slope and regression intercept.

4. The method of claim 3, in which the correcting step comprises:

capping or limiting the estimated interferent concentration so that the estimated mean interferent concentration is within ±3 standard deviations of historical mean concentration of the at least one interferent concentrations;

evaluating whether a historical coefficient of determination from the obtaining step at each of the plurality of time points that have been collected in a test sequence, for the one category of glucose magnitudes, is greater than a predetermined threshold;

if the evaluating step is true, applying a correction to the current output transient for each of the plurality of time points that has a historical coefficient of determination greater than the predetermined threshold; or if the evaluating step is false then selecting another time point and returning to the evaluating step.

5. The method of claim 4, in which the estimating of the at least one interferent is performed with an equation of the form:

$$EstimatedInterferent(GL_{Group}, t) = \frac{\text{Current}(GL_{Group}, t) - \text{Intercept}(GL_{Group}, t)}{\text{Slope}(GL_{Group}, t)}$$

where EstitnatedInterferent($GL_{Group}$, t) is determined for each glucose categorization group "$GL_{Group}$" and time point "t";

Current($GL_{Group}$, t) is obtained from the measuring step at the specified time point "t" for each glucose categorization group "$GL_{Group}$";

Intercept($GL_{Group}$, t) is obtained from historical data of regression analysis of historical transients based on the at least one interferent measurements at the specified time point "t" for each glucose categorization group "$GL_{Group}$";

Slope($GL_{Group}$, t) is obtained from historical data regression analysis of historical transients based on of the at least one interferent measurements at the specified time point "t" for each glucose categorization group "$GL_{Group}$"; and t includes any time point during the test sequence from about 0 second to about 5 seconds from a start of current output transient in the test sequence.

6. The method of claim 5, further comprising estimating an average interferent concentration based on all of the estimated interferent concentrations at selected time points "t" in which the correlation to the interferent and transient are the highest.

7. A method of determining an interferent concentration from a fluid sample with a glucose monitor and a biosensor, the method comprising the steps of:

depositing a physiological fluid sample in a test chamber of the biosensor to start a test sequence;

applying a plurality of potentials to electrodes disposed in the test chamber of the biosensor over a time interval of the test sequence;

measuring a current output transient over a plurality of time points during the time interval of the test sequence to provide a measured current output transient for each of the plurality of time points;

estimating a glucose concentration of a fluid sample from the measured current output transient of the measuring step;

categorizing the estimated glucose concentration into one of plural distinct categories of glucose magnitudes;

estimating a plurality of interferent concentrations at specific time points based on: (a) the measured current output transient; and (b) historical slopes and historical intercepts of current transient output for historical interferent concentrations that have been collected in the one category of glucose magnitudes;

determining an estimated mean interferent concentration from the plurality of estimated interferent concentrations from the estimating step; and annunciating the estimated mean interferent concentration in the sample.

8. The method of one of claim 1, 3, or 7, in which the estimating of the glucose concentration is obtained with an equation of the form:

$$G_{est} = \left(\frac{|i_r|}{|i_l|}\right)^p (a|i_{2CORR}| - zgr);$$

where: $G_{est}$ is the glucose concentration:

$$i_r = \sum_{t=4.4}^{t=5} i(t);$$

$$i_l = \sum_{t=1.4}^{t=4} i(t); \text{ and}$$

$$i_{2CORR} = \left(\frac{|i_{\approx 4.1secs}| + b|i_{\approx 5secs}| - c|i_{\approx 1.1secs}|}{|i_{\approx 4.1secs}| + b|i_{\approx 5secs}|}\right) i_r;$$

a is approximately 0.192, b is approximately 0.68, c is approximately 2, p is approximately 0.52, and zgr is approximately 2.

9. The method of one of claims 1 and 2, in which the calculating of the glucose concentration is performed after completion of the determining step for all of the plurality of time points during the time interval and is performed with an equation of the form:

$$G_{corr} = \left(\frac{|i_{rcorr}|}{|i_{lcorr}|}\right)^p (a|i_{2CORR}| - zgr);$$

where: $G_{corr}$ is the interferent corrected glucose concentration, $i_{rcorr}$ is a summation of corrected current transients, $i_{lcorr}$ is a summation of corrected current transients, $i_{corr\sim t}$ is a corrected current transient at each of the specified time points "t"

$$i_{rcorr} = \sum_{t=4.4}^{t=5} i(t);$$

$$i_{lcorr} = \sum_{t=1.4}^{t=4} i(t); \text{ and}$$

$$i_{2CORR} = \left(\frac{|i_{corr\approx 4.1secs}| + b|i_{corr\approx 5secs}| - c|i_{corr\approx 1.1secs}|}{|i_{corr\approx 4.1secs}| + b|i_{corr\approx 5secs}|}\right) i_{rcorr};$$

a is approximately 0.192, b is approximately 0.68, c is approximately 2, p is approximately 0.52, and zgr is approximately 2.

10. An analyte measurement system comprising:
a test strip including:
a substrate;
a plurality of electrodes disposed on the substrate and connected to respective electrode connectors; and
an analyte meter including:
a housing;
a test strip port connector configured to connect to the respective electrode connectors of the test strip; and
a microprocessor in electrical communication with the test strip port connector to apply electrical signals or sense electrical signals from the plurality of electrodes during a test sequence, the microprocessor is configured to: (a) apply a plurality of potential to electrodes disposed in the test chamber of the biosensor over a time interval of the test sequence; (b) measure a current output transient over a plurality of time points during the time interval of the test sequence to provide a measured current output transient for each of the plurality of time points; (c) estimate a glucose concentration of a fluid sample from the measured current output transient of the measuring step; (d) categorize the estimated glucose concentration into one of plural distinct categories of glucose magnitudes; (e) estimate a plurality of interferent concentrations at specific time points based on: (i) the measured current output transient; and (ii) historical slopes and historical intercepts of current transient output for historical interferent concentrations that have been collected in the one category of glucose magnitudes; (f) determine an estimated mean interferent concentration from the plurality of estimated interferent concentrations; (g) correct the measured current output transient based on: (i) the measured current output transient at the specific time points during the test sequence, (ii) the historical slope at the specific time points during the test sequence from historical data, and (iii) a historical mean interferent concentration from historical data and (iv) estimated mean interferent concentration; and (h) calculate a glucose concentration corrected for the presence of interferent based on the measured current output transient that includes the corrected current output transient at the specific time points.

11. The system of claim 10, in which the interferent comprises uric acid.

12. A method of determining glucose concentration corrected for effects of at least one interfering substance from a fluid sample with a glucose monitor and a biosensor, the method comprising the steps of:
ascertaining historical data relating to the at least one interfering substance in physiological fluid samples by:
determining a historical mean concentration for the at least one interfering substance including various standards of deviations from a plurality of physiological fluid samples measured separately by a referential sensor at various glucose concentrations;
storing the historical mean concentration and values of standard deviations from the mean of the at least one interfering substance of the plurality of physiological fluid samples;
measuring current output transient of each of the plurality of the physiological fluid samples with respect to time points during a test sequence; and obtaining historical regression of slopes and intercepts, along with coefficients of determination of the current output transient at corresponding time points with respect to a test interval for each sample of the plurality of samples; and retaining as historical data for each time point of the current transient of each of the physiological samples, the following parameters from regression analysis as a function of the at least one interfering substance concentration at each specific glucose concentration: (a) regression slope, (b) regression intercept, and (c) coefficient of determination associated with the regression slope and regression intercept;

depositing a physiological fluid sample in a test chamber of the biosensor to start a test sequence;

applying a plurality of potential to electrodes disposed in the test chamber of the biosensor over a time interval of the test sequence;

measuring a current output transient over a plurality of time points during the time interval of the test sequence to provide a measured current output transient for each of the plurality of time points;

estimating a glucose concentration of a fluid sample from the measured current output transient of the measuring step;

categorizing the estimated glucose concentration into one of plural distinct categories of glucose magnitudes;

estimating a plurality of at least one interfering substance concentration at specific time points based on: (a) the measured current output transient; and (b) historical slopes and historical intercepts of regression analysis of current transient output for at least one interfering substance historical concentrations that have been collected in the one category of glucose magnitudes;

determining an estimated mean at least one interfering substance concentration from the plurality of estimated at least one interfering substance concentrations from the estimating step;

correcting the measured current output transient based on: (a) the measured current output transient at the specific time points during the test sequence, (b) the historical slope at the specific time points during the test sequence from historical data, and (c) historical mean of the at least one interfering substance concentration and (d) estimated mean of the at least one interfering substance concentration of the estimating step; and calculating a glucose concentration corrected for the presence of at least one interfering substance based on the measured current output transient that includes the corrected current output transient at the specific time points from the correcting step.

13. The method of one of claim 1, 2, 7, or 12, in which the at least one interferent or the interfering substance comprises uric acid.

* * * * *